United States Patent [19]
Parsons et al.

[11] Patent Number: 5,518,887
[45] Date of Patent: May 21, 1996

[54] IMMUNOASSAYS EMPOLYING GENERIC ANTI-HAPTEN ANTIBODIES AND MATERIALS FOR USE THEREIN

[75] Inventors: Robert G. Parsons, Libertyville; Robert Kowal, Vernon Hills, both of Ill.

[73] Assignee: Abbott Laboratories, Abbott Park, Ill.

[21] Appl. No.: 160,110

[22] Filed: Dec. 1, 1993

Related U.S. Application Data

[63] Continuation-in-part of Ser. No. 859,772, Mar. 30, 1992, Pat. No. 5,270,166.

[51] Int. Cl.$^6$ .................................................. G01N 33/53
[52] U.S. Cl. .......................... 435/7.1; 435/7.2; 435/7.21; 435/7.31; 435/7.4; 436/520; 436/523; 436/525; 436/534; 436/807; 436/816; 436/817; 436/822; 436/901
[58] Field of Search ........................... 435/7.1, 7.2, 7.21, 435/7.4, 7.92, 7.31, 7.93, 7.94, 962, 973, 975; 436/518, 520, 523, 525, 524, 521, 531, 533, 536, 807, 808, 816, 817, 822, 815

[56] References Cited

U.S. PATENT DOCUMENTS

| | | | |
|---|---|---|---|
| 3,654,090 | 4/1972 | Schuurs et al. | |
| 4,185,084 | 1/1980 | Mochida et al. | 421/1 |
| 4,237,234 | 12/1980 | Meunier | 435/301 |
| 4,243,749 | 1/1981 | Sadeh et al. | 435/7 |
| 4,271,140 | 6/1981 | Bunting | 424/1 |
| 4,301,142 | 11/1981 | Enders | 424/8 |
| 4,308,026 | 12/1981 | Mochida et al. | 23/230 |
| 4,313,734 | 2/1982 | Leuvering | 23/230 |
| 4,342,739 | 8/1982 | Kakimi et al. | 424/1 |
| 4,373,932 | 2/1983 | Gribnau et al. | 436/501 |
| 4,419,453 | 12/1983 | Dorman et al. | 436/534 |
| 4,433,059 | 2/1984 | Chang et al. | 436/512 |
| 4,474,893 | 10/1984 | Reading | 436/547 |
| 4,668,640 | 5/1987 | Wang et al. | 436/536 |
| 4,678,331 | 7/1987 | Perry | 356/246 |
| 4,745,075 | 5/1988 | Hadfield et al. | 436/523 |
| 4,816,567 | 3/1989 | Cabilly et al. | 530/387 |
| 4,954,452 | 9/1990 | Yost et al. | 436/524 |
| 5,026,653 | 6/1991 | Lee et al. | 435/962 X |
| 5,075,100 | 12/1991 | Seno | 424/3 |
| 5,086,002 | 2/1992 | Hillyard et al. | 436/540 |
| 5,202,269 | 4/1993 | Ito et al. | 436/526 |
| 5,209,904 | 5/1993 | Forney et al. | 422/73 |
| 5,248,479 | 9/1993 | Parsons et al. | 422/58 |
| 5,252,459 | 10/1993 | Tarcha et al. | 435/6 |
| 5,270,166 | 12/1993 | Parsons et al. | 435/7.4 |

FOREIGN PATENT DOCUMENTS

| | | |
|---|---|---|
| 0105714 | 4/1984 | European Pat. Off. . |
| 0174195 | 3/1986 | European Pat. Off. . |
| 0177191A1 | 4/1986 | European Pat. Off. . |
| 0321736 | 6/1989 | European Pat. Off. . |
| 0351857 | 1/1990 | European Pat. Off. . |
| 0411945 | 2/1991 | European Pat. Off. . |
| 2084317 | 4/1982 | United Kingdom . |
| WO9208973 | 5/1992 | WIPO . |

OTHER PUBLICATIONS

S. G. Hadfield et al., "A novel coloured latex test for the detection and identification of more than one antigen", *Journal of Immunological Methods*, vol. 97(1987), pp. 153–158.

J. Kang et al., "A Highly Sensitive immunoenzymometric Assay Involving Common–Capture Particles and Membrane Filtration", *Clinical Chemistry*, vol. 32 (1986), pp. 1682–1686.

A. A. Hirata et al., "Passive Hemagglutination Procedures for Protein and Polysaccharide Antigens Using Erythrocytes Stabilized by Aldehydes", *The Journal of Immunology*, vol. 100 (1968), pp. 641–646.

G. Kohler et al., "Continuous cultures of fused cells secreting antibody of predefined specificity", *Nature*, vol. 256 (1975), pp. 495–497.

E. A. Kabat, et al, Experimental Chemistry, 1961 by Charles C. Thomas (Illinois) p. 122.

Seradyn, Inc., "Microparticle Immunoassay Techniques", 2nd Edition, 1988 pp. 4–6, 42–43.

*Primary Examiner*—David Saunders
*Assistant Examiner*—Susan C. Wolski
*Attorney, Agent, or Firm*—David L. Weinstein

[57] ABSTRACT

The present invention relates to immunoassay methods for detecting and measuring the amount of an analyte in a sample by means of generic anti-hapten antibodies. Also disclosed are multi-analyte immunoassay methods. Reagents, devices, and kits using the anti-hapten antibodies are also disclosed. The present invention also relates to immunoassay methods for detecting and measuring the amount of an analyte in a sample by means of a dual antibody format.

The present invention also relates to dyed erythrocytes, preferably fixed, which are coated with antibodies. Also disclosed is the use of these dyed erythrocytes in agglutination assays to detect and measure the presence of an analyte in a sample. The analyte can be a hapten, an antigen, or an antibody. Also included are agglutination assays, compositions and kits using these dyed and coated erythrocytes.

18 Claims, 9 Drawing Sheets

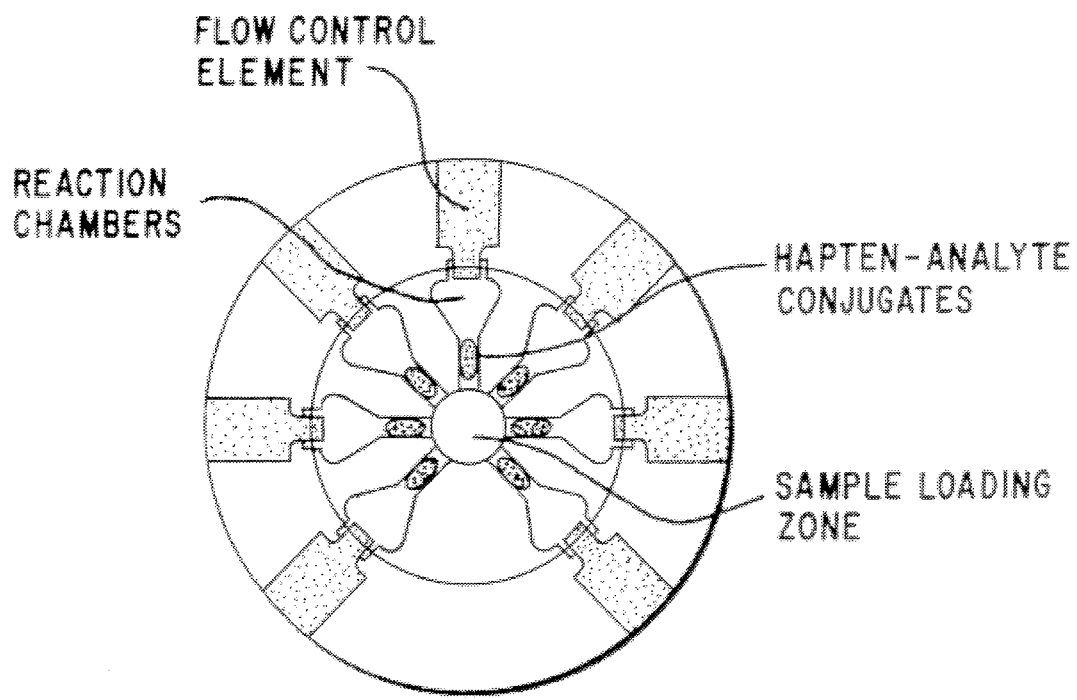
FIG. 3A
FIG. 3B
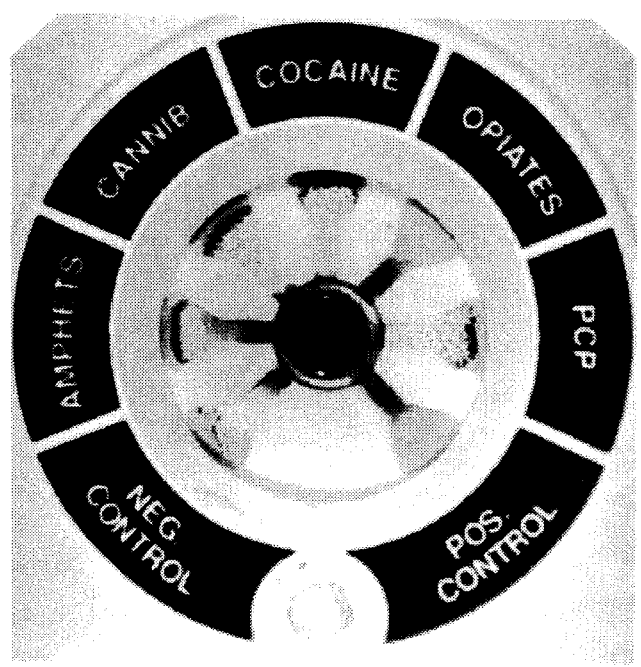

IMMUNOASSAYS EMPOLYING GENERIC ANTI-HAPTEN ANTIBODIES AND MATERIALS FOR USE THEREIN

This application is a continuation-in-part of U.S. patent application Ser. No. 07/859,772 filed Mar. 30, 1992, now U.S. Pat. No. 5,270,166, entitled "IMMUNOASSAYS EMPLOYING GENERIC ANTI-HAPTEN ANTIBODIES AND MATERIALS FOR USE THEREIN", which enjoys common ownership and is incorporated herein by reference. Also incorporated by reference are U.S. patent applications Ser. No. 138,253, filed on Dec. 23, 1987, entitled "Agglutination Reaction Device" to Parsons, R. G., et al.; Ser. No. 614,762, filed Nov. 16, 1990, entitled "Improved Agglutination Reaction Device Utilizing Selectively Impregnated Material", to Forney, R. J., et al.; Ser. No. 614,895, filed Nov. 16, 1990, entitled "Improved Agglutination Reaction Device Utilizing Porous Absorbent Material" to Ropella, P. J., et al; and Ser. No. 614,817, filed Nov. 16, 1990,"Improved Agglutination Reaction Device Having Geometrically Modified Chambers", to Parsons, R. G. et al.

FIELD OF THE INVENTION

This invention relates to the field of immunoassays.

BACKGROUND OF THE INVENTION

In-vitro diagnostic tests via immunoassays typically involve antibodies with specific binding affinity toward the analytes of interest. In such test configurations, antigenic analytes either bind directly with the antibody or compete with a hapten-label conjugate (competition assay).

In the former case, the antibody-antigen complex may be allowed to grow as in agglutination assays. Alternatively, in sandwich assays, another antibody with affinity to the antigen can be conjugated to a signal label and allowed to bind the primary antibody-antigen complex. The signal response is directly proportional to the analyte concentration.

In competition assays, competition is established between the analytes, typically small molecules in nature, and the hapten-label conjugates. The signal response is inversely proportional to the analyte concentration.

Most target analytes can, in principle, be detected using either the competition assay or the sandwich assay format. While there are numerous examples where the stated methods served the purpose very well, the utility of these approaches however, were somewhat limited in that a single assay is specific for a single analyte only. A multi-analyte assay is difficult.

The following exemplifies the different available immunoassay formats. U.S. Pat. No. 4,185,084 to Mochida et al., discloses non-homogeneous assays with wash and separation steps. An insolubilized anti-analyte antibody acts as a primary capture phase for the analyte which is conjugated to a hapten (hapten-analyte conjugate). After washing, soluble labelled anti-hapten antibody is added and the complex of (anti-analyte antibody/hapten-analyte conjugate/anti-hapten antibody) is detected. U.S. Pat. No. 4,243,749, to Sadeh et al., discloses another similar sandwich assay format. Sadeh et al., is specifically oriented towards measuring low molecular weight (hapten) antigens. The unknown analyte and the hapten-analyte conjugate are incubated together with the insoluble anti-analyte antibody in a competitive assay format. Following the wash step, soluble labeled anti-hapten antibody is added and the system is washed again and the labeled complex of (anti-analyte antibody/hapten-analyte conjugate/anti-hapten antibody) detected.

Kang et al., *Clin. Chem.*, 32(9):1682–1686 (1986) describes two assay formats. The first assay format presents an enzyme immunoassay which uses an anti-hapten antibody coated microparticle (the common capture particle), an anti-analyte antibody conjugated to a hapten (hapten-anti-analyte-antibody conjugate), and a labeled anti-analyte antibody. If the analyte is present in a sample, a complex of (anti-hapten antibody coated microparticle/hapten-anti-analyte-antibody conjugate/analyte/labeled anti-analyte antibody) is formed and detected. Fluorescein serves as the capture hapten. The microparticle is a latex particle.

Kang et al.'s second assay format is similar to that of Bunting, U.S. Pat. No. 4,271,140. The assay format consists of an anti-hapten antibody bound to a solid phase, a hapten conjugated to an anti-analyte antibody (hapten-anti-analyte antibody) and labeled analyte. The complex of all three components are detected.

In agglutination assays, either the antibodies or the antigens (or hapten) may be bound to small particles. The particles that have been used as agglutable carriers include latex, charcoal, kaolinite, bentonite, inorganic colloidal particles, as well as both microbial cells and erythrocytes. See Mochida, U.S. Pat. No. 4,308,026. When these coated particles (coated with either antibodies or antigens) are mixed with samples containing antigens or antibodies, the coated particles would form visually detectable agglutination. Agglutination is characterized by the clumping of the latex polymer particles from an otherwise smooth suspension. Qualitative latex agglutination tests can be carried out on a simple slide without the aid of any instrumentation. More than one antigen can be detected simultaneously by means of differently colored latex particles which have each been sensitized with antibodies of different specificity and then mixed together. Hadfield, S. G., et al., *J. Immunol Methods*, 97:153–8 (1987). U.S. Pat. No. 4,745,075 to Hadfield et al, May 17, 1988. U.S. Pat. No. 4,419,453 further discloses latex particles dyed with Amocid yellow, brilliant crocein 3BA red dye, and Calco Oil Blue N Dye. U.S. Pat. No. 4,745,075 discloses that there are also marketed test kits for the grouping of Beta Haemolytic Streptococci which include reagents in which the solid phase is a suspension of killed red-dyed or blue-dyed *Staphylococcus aureus* cells.

Hillyard et al., U.S. Pat. No. 5,086,002, discloses an erythrocyte agglutination assay in which the agglutination reagent comprises at least one erythrocyte binding molecule coupled to at least one specific analyte binding molecule wherein the erythrocyte binding molecule does not cause agglutination when incubated with erythrocytes in the absence of analyte (in the case of a direct assay) or analyte binding reagent (in the case of an indirect assay). The erythrocytes are preferably endogenous to the blood sample to be tested. Mixtures of conjugates and conjugates of analyte analogues with erythrocyte binding molecules may also be used as agglutination reagents. Chang, U.S. Pat. No. 4,433,059, discloses an agglutination immunoassay reagent in which two antibodies are covalently linked "tail-to-tail", so as not to alter their specificity. One antibody is specific for an antigen borne by an indicator substance, such as an erythrocytes.

Antibodies or antisera which are used in immunoassays sometimes show reactivity to compounds which are distinct from the antigen for which the antibody was originated. This reactivity, termed cross reactivity, is usually directed against compounds which are structurally related to the primary antigen. This cross reactivity may be undesireable because structurally similar, but non-related molecules are recognized by the antibody. This reduces the apparent specificity of the antibody and therefore reduces the specificity of any diagnostic test which uses that antibody. Diagnostic tests fail to teach a method for mixing two or more antibodies (antisera) which each have different patterns of cross reactivity, to obtain a common antibody pool which does not display the cross reactivity of either of the original antibodies.

SUMMARY OF THE INVENTION

One aspect of the invention presents an immunoassay for an analyte (A). The immunoassay uses an anti-hapten antibody ($\alpha$H), a hapten conjugated to an analyte (H-A), and an anti-analyte antibody ($\alpha$A). If the analyte is not present in the sample, a complex of $\{(\alpha H)(H-A)(\alpha A)\}$ is formed. If the analyte is present in the sample, the analyte will compete with (H-A) for ($\alpha$A), to form the complex of $\{(\alpha A)(A)\}$. After an appropriate incubation period, the presence of $\{(\alpha H)(H-A)(\alpha A)\}$ or $\{(\alpha A)(A)\}$ is detected or measured. The amount of $\{(\alpha H)(H-A)(\alpha A)\}$ is inversely proportional to the amount of analyte in the sample, whereas the amount of $\{(\alpha A)(A)\}$ is directly proportional to the presence of the analyte in the sample.

The above assay can be presented in an agglutination assay format wherein the anti-hapten antibody is coated onto a particle, preferably a microparticle. In this case, a separation step is not required. The formation of the complex of $\{(\alpha H)(H-A)(\alpha A)\}$ can be visually detected in the agglutination of the coated particles.

Another embodiment of the present invention presents methods of improved immunoassays utilizing a dual antibody format. The dual antibody format tests for the presence of an analyte (A) in a test sample with the use of at least one other antibody ($\alpha$B) with a different specificity for analyte (A). The dual antibody format can detect or measure the amount of an analyte (A) in the presence of interfering substances (X) in the test sample. The analyte or an analyte analog (A) can be attached directly or indirectly to a solid phase, e.g., a microparticle. The amount of complexes $\{(P-A)(\alpha A)\}$, or $\{(P-A)(\alpha B)\}$, or $\{(P-A)(\alpha A)(\alpha B)\}$, or combinations of the three complexes is inversely proportional to the amount of analyte (A) in the test sample.

Another embodiment of present invention uses an anti-hapten antibody ($\alpha$H) attached to a microparticle, a hapten conjugated to an analyte (H-A), and two or more anti-analyte (A) antibodies ($\alpha$A) and ($\alpha$B). The amount of complexes $\{(\alpha H)(H-A)(\alpha A)\}$, or $\{(\alpha H)(H-A)(\alpha B)\}$, or $\{(\alpha H)(H-A)(\alpha A)(\alpha B)\}$, or combinations of the three complexes is inversely proportional to the amount of analyte (A) in the test sample.

Another aspect of the invention presents the preceding agglutination assays with the addition of particles not coated with the anti-hapten antibodies, the color of the coated and uncoated particles are such that they enhance visualization of the agglutination or lack thereof.

Another aspect of the invention presents multi-analyte assays which employ anti-hapten antibodies attached to a solid phase, and the solid phase is preferably a particle. The multi-analyte assays can be conducted in competitive agglutination assay formats.

Another aspect of the invention presents reagents and kits for conducting the above assays.

Another aspect of the invention presents a multi-analyte assay device with different chambers, wherein each chamber contains a reagent for a specific analyte, and the reagent is a hapten conjugated to the specific analyte to be assayed.

Another aspect of the invention presents dyed and preferably fixed erythrocytes which have been coated with anti-hapten antibodies, and can be used in agglutination assays. Also presented are: agglutination assay kits containing the dyed and coated erythrocytes, and compositions comprising dyed and coated erythrocytes for use in agglutination assays.

BRIEF DESCRIPTION OF DRAWINGS

FIGS. 3A and 3B illustrate an example of a multi-analyte assay device.

FIG. 6 illustrates the situation where there is an absence of analyte in the dual antibody format. Therefore both antibodies in the dual antibody format form the agglutination reaction.

FIG. 7 illustrates the situation where structurally related substances present in the test sample can be bound by one of the antibodies in the dual antibody format and still get agglutination.

FIG. 8 illustrates the situation where a different structurally related substance can be bound by the other antibody in the dual antibody format and still get agglutination.

FIG. 9 illustrates the situation where analyte is present in the test sample. Both antibodies in the dual antibody format bind the analyte and no agglutination occurs.

DETAILED DESCRIPTION OF THE INVENTION

Figure 1:
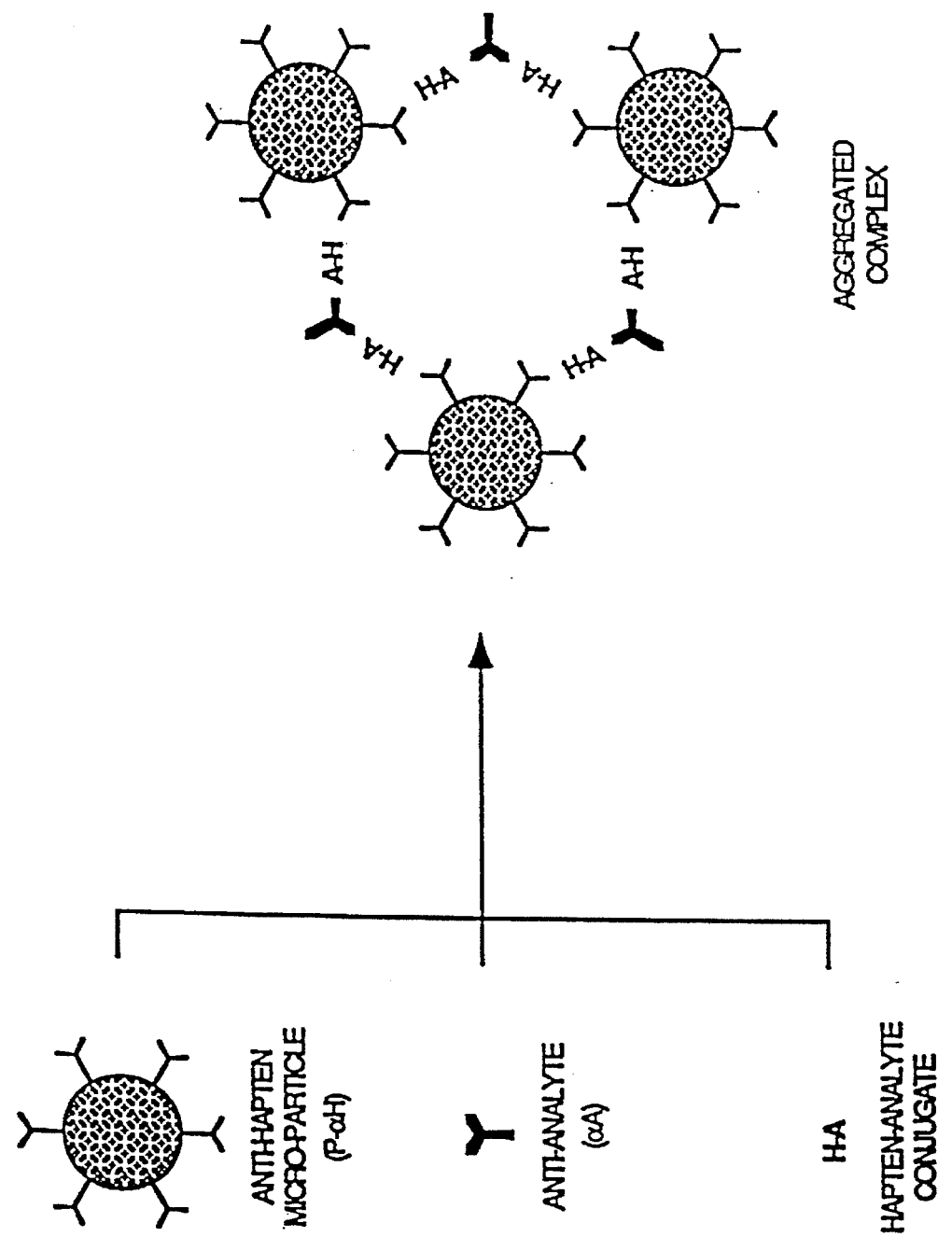
FIG. 1 illustrates the agglutination of anti-hapten microparticles in the absence of analytes.

The invention presents an immunoassay for an analyte (A). The immunoassay uses an anti-hapten antibody ($\alpha$H), a hapten conjugated to an analyte (H-A), and an anti-analyte antibody ($\alpha$A). The ($\alpha$A) can be labelled to allow for detection. If the analyte is not present in the sample, a complex of $\{(\alpha H)(H-A)(\alpha A)\}$ is formed. If the analyte is present in the sample, the analyte will compete with (H-A) for ($\alpha$A), to form the complex of $\{(\alpha A)(A)\}$. After an appropriate period of incubation, the complex of $\{(\alpha H)(H-A)(\alpha A)\}$ is then separated from the uncomplexed (H-A), ($\alpha$A), or the complex of $\{(\alpha A)(A)\}$, if any. The presence of $\{(\alpha H)(H-A)(\alpha A)\}$ or $\{(\alpha A)(A)\}$ is then detected or measured. The amount of $\{(\alpha H)(H-A)(\alpha A)\}$ is inversely proportional to the amount of analyte in the sample, whereas the amount of $\{(\alpha A)(A)\}$ is directely proportional to the presence of the analyte in the sample.

The above assay can be conducted in a competitive assay format, whereby the anti-hapten antibody can be attached to a solid phase.

The above assay can also be presented in an agglutination assay format wherein the anti-hapten antibody is coated onto a particle, preferably a microparticle. In agglutination assays, no separation steps are required. The formation of the complex of {(αH)(H-A)(αA)} can be visually detected in the agglutination of the coated particles.

The invention also presents methods of improved immunoassays for an analyte (A) with the use of at least one other antibody (αB) with a different specificity for analyte (A) in the presence of interfering substances (X). The use of at least one other antibody (αB), creates a dual antibody format for detecting the presence or quantifying the amount of analyte (A) in the presence of interfering substances in a test sample. Such interfering substances can be structurally related substances which the antibodies in the dual antibody format show some level of cross reactivity. The dual antibody format can also utilize an anti-hapten antibody (αH), a hapten conjugated to an analyte (H-A), and at least two anti-analyte (A) antibodies (αA) (αB).

According to one embodiment of the dual antibody format, a method of utilizing at least two antibodies (αA and αB) with different specificities for analyte (A) is employed. If the analyte (A) is not present in the test sample, an agglutination reaction occurs due to the interaction of the anti-hapten antibody (αH), hapten-analyte conjugate (H-A), and the antibodies (αA and αB) with different specificities for analyte (A). The antibodies (αA and αB) specific for analyte (A) bind the analyte in the conjugate and accordingly, the complexes formed are {(αH)(H-A)(αA)}, or {(αH)(H-A)(αB)}, or {(αH) (H-A)(αA)(αB)} or combinations of the three complexes. The amount of complexes is inversely proportional to the amount of analyte (A) in the test sample.

According to another embodiment of the dual antibody format, the analyte (A) is detected when it is present in the test sample. The analyte (A) will compete with (H-A) for (αA and (αB), to form the complexes of {(αA)(A)} and {(αB)(A)}. The presence of {(αH)(H-A)(αA)}, or {(αH)(H-A)(αB)}, or {(αH)(H-A)(αA)(αB)} or combinations of the three complexes is detected or measured. The amount of {(αH)(H-A)(αA)}, or {(αH)(H-A)(αB)}, or {(αH)(H-A)(αA)(αB)}, or combinations of the three complexes is inversely proportional to the amount of analyte (A) in the sample, whereas the amount of {(αA)(A)} and {(αB)(A)} is directly proportional to the presence of the analyte (A) in the sample. If there is sufficient amounts of analyte (A) in the sample, after an appropriate period of incubation, the analyte (A) will have competed sufficiently to bind the anti-analyte (A) antibodies to give complexes {(αA)(A)} and {(αB)(A)} thereby limiting formation of the complexes {(αH)(H-A)(αA)}, or {(αH)(H-A)(αB)}, or {(αH) (H-A)(αA)(αB}.

According to another embodiment of the dual antibody format, the analyte (A) is not present in the test sample. A structurally related substance (X) to analyte (A) can be present which (αB) has specificity for but which (αA) does not. In such a scenario, the structurally related substance (X) binds (αB) while (αA) forms the complex {(αH)(H-A)(αA)}. Subsequent separation of the complexes and detection can occur.

According to another embodiment of the dual antibody format, the analyte (A) is not present in the test sample. A structurally related substance (X) to analyte (A) can be present which (αA) has specificity for but (αB) does not. In such a scenario, the structurally related substance (X) binds (αA) while (αB) forms the complex {(αH)(H-A)(αB)}. Subsequent separation of the complexes and detection can occur.

The above assays in the dual antibody format can be conducted in a competitive assay format as described above.

The above assays can also be presented in an agglutination assay format. Both competitive and agglutination assay formats can be presented whereby the anti-hapten antibody (αH) can be coated or attached to a particle, preferably a microparticle. In agglutination assays, no separation steps are required. The formation of the complexes {(αH)(H-A)(αA)}, {(αH)(H-A)(αB)}, {(αH)(H-A)(αA)(αB)}, or combinations of the three complexes can be visually detected in the agglutination of the coated particles. Moreover, the addition of (αB) to the assay allows for the detection or measurement of an amount of analyte (A) in a test sample containing interfering substance (X) which one of either anti-analyte antibodies (αA) or (αB) show cross reactivity to the interfering substance (X), thereby preserving assay integrity by eliminating false positives.

Also disclosed is a direct agglutination assay for the analyte with multiple epitopes using particles coated with anti-hapten antibodies (P-αH), conjugates of hapten and antibodies against the analyte (H-αA), the degree of agglutination of the coated particles is directly proportional with the presence of the analyte in the sample.

Also disclosed herein is an immunoassay method for detecting and measuring an antibody (αA) in a sample, by exposing the sample to anti-hapten antibodies (αH), and hapten conjugated to antigen to which the antibody binds (H-Ag), and labeled antibody (αA*). The resulting complex of {(αH)(H-Ag)(αA*)}, if any, is inversely proportional to the amount of the antibody (αA) in the sample, and the amount of remaining (αA*) is directly proportional to the amount of (αA) in the sample.

Also disclosed herein is a direct agglutination assay for antibodies (αA) in a sample, which exposes the sample to particles coated with anti-hapten antibodies (P-αH), and conjugates comprising haptens and antigens to the antibodies (H-Ag). Agglutination of the coated particles is directly proportional to the amount of antibodies in the sample.

Also disclosed herein are multi-analyte assays and assay devices which employ anti-hapten antibodies. Reagents and kits for conducting all the above assays, for example dyed fixed erythrocytes coated with anti-hapten antibodies, are also disclosed herein.

Assay Formats

The invention can be practiced in formats that include: homogenous, sandwich, competitive, and agglutination assay formats. In the sandwich or competitive assay formats, the anti-hapten antibodies can be attached to a solid phase, thus rendering the solid phase into a generic solid phase that can be used to assay different analytes. Materials for solid phase can be any of those used for immunoassays. Natural, synthetic or naturally occurring materials that are synthetically modified can be used. They include: polysaccharides, e.g., cellulose materials including paper, cellulose and cellulose derivatives such as cellulose acetate and nitrocellulose; silica; fiberglass; inorganic materials such as deactivated alumin, diatomaceous earth or other inorganic finely divided material uniformly dispersed in a porous polymer matrix made of polymers such as vinyl chloride, vinyl chloride-propylene copolymer, and vinyl chloride-vinyl acetate copolymer; cloth, both naturally occurring (e.g., cotton) and synthetic (e.g., nylon); porous gels such as silica gel, agarose, dextran and gelatin; polymeric films such as polyacrylamide; magnetic particles; microtitre plates; polystyrene tubes; protein binding membranes; agarose; Sephadex (Pharmacia Fine Chemicals, Inc., Piscataway, N.J.); Trisacryl (Pointet-Girard, France); silicon particles; porous fibrous matrixes etc.

One embodiment of the invention presents a competitive assay format wherein the sample for which the analytes are to be assayed is mixed with hapten-analyte conjugate (H-A) and antibodies to the specific analytes to be assayed (anti-analyte antibodies, ($\alpha$A). The anti-analyte antibodies are labeled for detection, e.g. with enzyme, radioactive, fluorescent, or chemical labels. The mixture is then passed over the solid phase, to which anti-hapten antibodies have been attached, and incubated for a sufficient time to allow the complex of $\{(\alpha H)(H-A)(\alpha A)\}$ to form. Next, the unbound reagents are separated, e.g. the unbound reagents are dissolved in an aqueous medium and washed away from the solid phase and the formation of the complex of $\{(\alpha H)(H-A)(\alpha A)\}$ on the solid phase is detected by detecting the labeled ($\alpha$A). If the analyte is not present, the complex will be present. If the sample contains the analytes, the analytes will bind the labeled anti-analyte antibodies, and no complex will be present, or the amount of complexes will be reduced. Thus, the presence of the complex is-inversely proportional to the analyte concentration in the sample. Alternatively, one can assay for the presence of the remaining unbound labelled ($\alpha$A) in the aqueous medium. Methods for conducting a competitive assay, including the wash step, are well known in the art, see e.g. Mochida et al., U.S. Pat. No. 4,185,084. An example of the competitive assay format is shown below in Example 13.

Another embodiment of the present invention presents a dual antibody format for detecting the presence or measuring an amount of an analyte (A). The dual antibody format involves the method of utilizing two or more antibodies ($\alpha$A and $\alpha$B) of different specificities for analyte (A). This detection or measurement can occur in the presence of interfering substances (X). Such interfering substances (X) can be structurally related substances to which one of the antibodies ($\alpha$A or $\alpha$B) in the dual antibody format can show some degree of cross reactivity. In this embodiment, the analyte (A) is attached directly or indirectly to a particle, e.g., a microparticle, to form a microparticle-analyte (P-A). If the analyte (A) and a structurally related analyte (X) are not present in the test sample, an agglutination reaction occurs due to complex formation between the microparticle-analyte conjugate (P-A) and the antibodies ($\alpha$A and $\alpha$B). The analyte can be attached to the microparticle either directly or indirectly. Techniques and procedures of coating the microparticles are known to those skilled in the art.

According to another embodiment of the dual antibody format, the analyte (A) is detected when it is present in the test sample. The analyte (A) will compete with (P-A) for ($\alpha$A) and ($\alpha$B), to form the complexes of $\{(\alpha A)(A)\}$ and $\{(\alpha B)(A)\}$. After an appropriate period of incubation, the complexes, if any, of $\{(P-A)(\alpha A)\}$, or $\{(P-A)(\alpha B)\}$, or $\{(P-A)(\alpha A)(\alpha B)\}$ or combinations of the three complexes is then separated from the complexes of $\{(\alpha A)(A)\}$ and $\{(\alpha B)(A)\}$. The presence of any of the complexes can then be detected or measured. The amount of $\{(P-A)(\alpha A)\}$, or $\{(P-A)(\alpha B)\}$, or $\{(P-A)(\alpha A)(\alpha B)\}$ or combinations of the three complexes is inversely proportional to the amount of analyte (A) in the test sample, whereas the amount of $\{(\alpha A)(A)\}$ and $\{(\alpha B)(A)\}$ is directly proportional to the presence of the analyte (A) in the test sample. If there is sufficient amounts of analyte (A) in the test sample, after an appropriate period of incubation, the analyte will have competed sufficiently to bind the anti-analyte antibodies ($\alpha$A and $\alpha$B) to give complexes $\{(\alpha A)(A)\}$ and $\{(\alpha B)(A)\}$ to effectively prevent enough formation of the complexes $\{(P-A)(\alpha A)\}$, or $\{(P-A)(\alpha B)\}$, or $\{(P-A)(\alpha A)(\alpha B)\}$ or combinations of the three.

Another embodiment of the dual antibody format includes the situation whereby the analyte (A) is not present in the test sample. A structurally related substance (X) can be present which ($\alpha$A) has specificity for but which ($\alpha$B) does not. In such an example, the structurally related substance (X) binds ($\alpha$A) and forms a complex $\{(\alpha A)(X)\}$ while ($\alpha$B) forms the complex $\{(P-A)(\alpha B)\}$. Even if there is sufficient amounts of structurally related analyte (X) to bind all of the antibody ($\alpha$A), antibody ($\alpha$B) will still form a complex with (P-A). Subsequent separation of the complexes and detection of the reaction gives a negative reaction for the analyte (A).

According to another embodiment of the dual assay format, the analyte (A) is not present in the sample. A structurally related substance (X) can be present which ($\alpha$B) has cross reactivity for but which ($\alpha$A) does not. The antibody ($\alpha$B) cross reacts with structurally related substance (X) while ($\alpha$A) forms the complex $\{(P-A)(\alpha A)\}$.

Another aspect of the present invention presents a dual antibody format for detecting the presence or measuring an amount of an analyte (A). The dual antibody format involves the method of utilizing two or more antibodies ($\alpha$A and $\alpha$B) of different specificities for analyte (A). This detection or measurement can occur in the presence of interfering substances (X). Such interfering substances (X) can be structurally related substances to which one of the antibodies ($\alpha$A or $\alpha$B) in the dual antibody format can show some degree of cross reactivity. If the analyte (A) and a structurally related analyte (X) are not present in the sample, an agglutination reaction occurs due to complex formation between the anti-hapten antibody ($\alpha$H), hapten-analyte conjugate (H-A), and the antibodies $\alpha$A and $\alpha$B. The antibodies specific for analyte (A) bind the analyte in the conjugate thereby allowing agglutination of the complexes. Accordingly the complexes formed in the agglutination reaction are $\{(\alpha H)(H-A)(\alpha A)\}$, or $\{(\alpha H)(H-A)(\alpha B)\}$, or $\{(\alpha H)(H-A)(\alpha A)(\alpha B)\}$ or combinations of the three complexes. One or both anti-analyte antibodies ($\alpha$A and $\alpha$B) can be labelled for detection, e.g. with enzyme, radioactive, fluorescent, or chemical labels.

The antibodies in the dual antibody format can be either monoclonal or polyclonal. The preferred embodiment is where the second antibody is a monoclonal. It is also to be understood that more than two antibodies with different specificities to an analyte (A) can be utilized. For example, a third antibody ($\alpha$C) with a different specificity to an analyte (A) may be added to to the assay to improve specificity. In one such example, there would be more than one interfering substance (X) present in the test sample which antibodies ($\alpha$A and $\alpha$B) show cross reactivity to thereby necessitating the third antibody ($\alpha$C) to form the agglutination of complex $\{(\alpha H)(H-A)(\alpha C)\}$. Additionally, the third antibody ($\alpha$C) can be added to bind an interfering substance (X) even if the interfering substance would not prevent agglutination of complexes by either or both antibodies ($\alpha$A or $\alpha$B). In addition, any additional antibodies added in the dual antibody format,e.g.,($\alpha$C), can be either polyclonal or monoclonal, more preferably monoclonal.

According to another embodiment of the dual antibody format, the analyte (A) is detected when it is present in the test sample. The analyte (A) will compete with (H-A) for ($\alpha$A) and ($\alpha$B), to form the complexes of $\{(\alpha A)(A)\}$ and $\{(\alpha B)(A)\}$. After an appropriate period of incubation, the complexes, if any, of $\{(\alpha H)(H-A)(\alpha A)\}$, or $\{(\alpha H)(H-A)(\alpha B)\}$, or $\{(\alpha H)(H-A)(\alpha A)(\alpha B)\}$ or combinations of the three complexes is then separated from the complexes of $\{(\alpha A)(A)\}$ and $\{(\alpha B)(A)\}$. The presence of any of the complexes can then be detected or measured. The amount of $\{(\alpha H)(H-A)(\alpha A)\}$, or $\{(\alpha H)(H-A)(\alpha B)\}$, or $\{(\alpha H)$ (H-A)(αA)(αB)} or combinations of the three complexes is inversely proportional to the amount of analyte (A) in the test sample, whereas the amount of {(αA)(A)} and {(αB)(A)} is directly proportional to the presence of the analyte (A) in the test sample. If there is sufficient amounts of analyte (A) in the test sample, after an appropriate period of incubation, the analyte will have competed sufficiently to bind the anti-analyte antibodies (αA and αB) to give complexes {(αA)(A)} and {(αB)(A)} to effectively prevent enough formation of the complexes {(αH)(H-A)(αA)}, or {(αH)(H-A)(αB)}, or {(αH) (H-A)(αA)(αB)} or combinations of the three. Accordingly, in such an example the assay gives a positive result upon detection. For example, if phencyclidine (PCP) is the analyte (A), then antibody (αA) would be (αPCP1) and (αB) would be (αPCP2). Both antibodies (αPCP1 and αPCP2) have different specificities for PCP. Therefore, both antibodies will bind PCP and the presence of complexes {(αH)(H-PCP)(αPCP1)}, or {(αH)(H-PCP)(αPCP2)}, or {(αH)(H-PCP)(αPCP1)(αPCP2)} or combinations of the three complexes is inversely proportional to the amount of PCP in the sample, whereas the amount of {(αPCP1)(PCP)} and/or {(αPCP2)(PCP)} is directly proportional to the amount of the PCP in the test sample.

Yet, another embodiment of the dual antibody format includes the situation whereby the analyte (A) is not present in the test sample. A structurally related substance (X) can be present which (αA) has specificity for but which (αB) does not. In such an example, the structurally related substance (X) binds (αA) and forms a complex {(αA)(X)} while (αB) forms the complex {(αH)(H-A)(αB)}. Even if there is sufficient amounts of structurally related analyte (X) to bind all of the antibody (αA), antibody (αB) will still form a complex with (H-A) and (αH). Subsequent separation of the complexes and detection of the reaction gives a negative reaction for the analyte (A). For example, the structuraly related substance (X) can be the methadone metabolite 2-ethylidene-1,5-dimethyl-3,3-diphenylpyrrolidine (EDDP) and the analyte (A) can be PCP. Both antibodies (αA antibody would be αPCP1 and αB would be αPCP2) have different specificities to an analyte (PCP) while (αPCP1) has crossreactivity to structurally related substance (EDDP). Therefore, the presence of (EDDP) in the test sample causes (αPCP1) to bind EDDP thereby leaving (αPCP2) to form the complex {(αH)(H-PCP)(αPCP2)}. The amount of complex {(αH)(H-PCP)(αPCP2)} formed is inversely proportional to the amount of analyte (PCP) in the test sample.

According to another embodiment of the dual assay format, the analyte (A) is not present in the sample. A structurally related substance (X) can be present which (αB) has cross reactivity for but which (αA) does not. The antibody (αB) cross reacts with structurally related substance (X) while (aA) forms the complex {(αH)(H-A)(αA)}. For example, the structurally related substance (X) can be dextromethorphan and the analyte (A) can be PCP. Both antibodies (αA antibody would be αPCP1 and αB would be αPCP2) have different specificities to the analyte (PCP) while (αPCP2) has crossreactivity to structurally related substance, dextromethorphan. Therefore, the presence of dextromethorphan in the test sample causes (αPCP2) to bind dextromethorphan while (αPCP1) forms the complex of {(αH)(H-PCP) (αPCP1)}. The amount of complex {(αH)(H-PCP)(αPCP1)} formed is inversely proportional to the amount of analyte (PCP) in the test sample.

Analytes suitable for detection and/or measurement by the dual antibody format include low molecular weight substances, e.g., steroids such as testosterone, steriol, progesterone, corticosterone, aldosterone; thyroid hormones such as thyroxine and triiodothyronine; physiologically active peptides e.g. bradykinin, angiotensin, thyroid hormone-releasing hormone, and luteinizing hormone-releasing hormone; physiologically active amines such as epinephrine, norepinephrine, histamine, and serotonin; prostaglandin; relatively low molecular weight substances, e.g., insulin, glucagon, adrenocorticotropic hormone, and gastrin; and high molecular weight substances, e.g., human chorionic gonadotropin, growth hormone, human placental lactogen, immunoglobulin E, alpha-fetoprotein, hepatitis B antigen. The analyte can be a hapten, an antigen, or an antibody. Examples of antigens include antigens of micro-organisms such as human immunodeficiency virus (HIV) antigens, tumor-specific antigens, cell or tissue antigens, and serum antigens. The analyte is preferably small molecules such as therapeutic drugs, drugs of abuse, and toxins.

The dual antibody format assays can be conducted in a competitive assay format as described above. The dual antibody format assays can also be presented in an agglutination assay format. In one embodiment of the dual antiboby format, an analyte or an analyte analog can be attached directly or indirectly to a particle, e.g., a microparticle. Another embodiment of the dual antibody format can be conducted in both competitive and agglutination assay formats whereby the anti-hapten antibody is coated onto a particle, preferably a microparticle. In agglutination assays, no separation steps are required. The formation of the complexes {(αH)(H-A)(αA)}, {(αH)(H-A)(αB)}, {(αH)(H-A)(αA)(αB)}, or combinations of the three can be visually detected in the agglutination of the coated particles. Moreover, the addition of (αB) to the assay allows for the detection or measurement of an amount of analyte (A) in a test sample containing interfering substance (X).

As mentioned, the above approaches can be applied to agglutination assays. Currently, to test different analytes, especially in agglutination assay format, a specific set of reagents have to be made for each of the analytes. This not only increases the cost of manufacturing, but also makes it impossible to perform a single multi-analyte test. The present invention presents the following advantages:

1) The anti-hapten coated particle (P-αH) is a generic reagent, which can be used in a variety of tests.

2) The assay format makes it possible to run multi-analyte tests, i.e. to perform multiple tests simultaneously with a single specimen.

3) The use of at least two antibodies with different specificities for analyte (A) can be utilized in the multi-analyte test format to reduce nondesirable cross reactivity.

Compared to the prior art agglutination immunoassays discussed in the Background of the Invention, the present invention offers the advantages of simplicity, rapidity, clarity, economy, sensitivity and specificity. The agglutination assays presented here allow for visual detection of the result and do not involve wash and separation steps. Whereas the prior art agglutination assays require particles that are sensitized to the specific analyte to be detected and do not provide for multi-analyte tests; the present invention allows for the performance of multi-analyte tests with a single specimen, and the use of a generic reagent for different tests.

Figure 5:
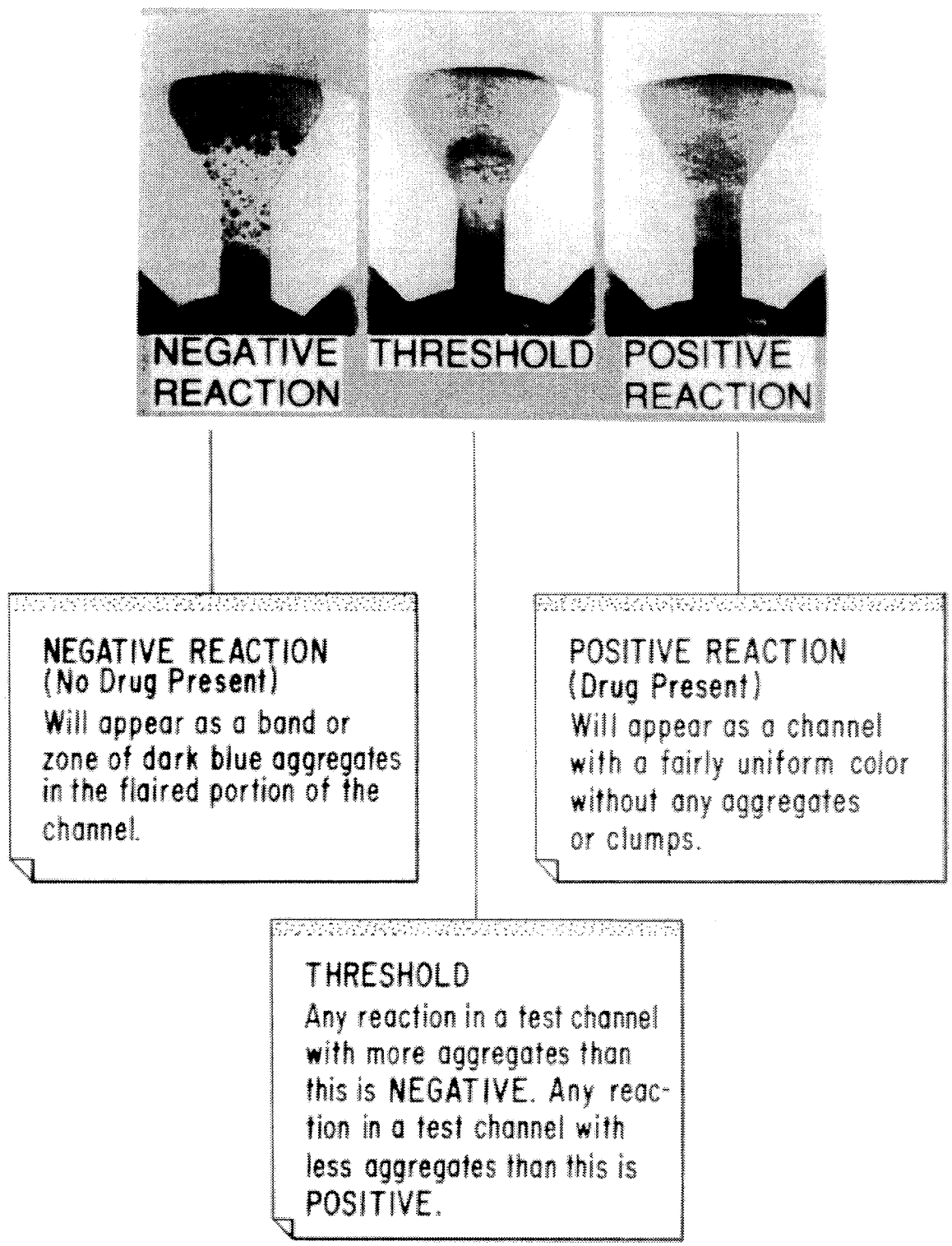
FIG. 5 presents photographs of the negative, threshold, and positive reactions in drug assays.
Figure 6:
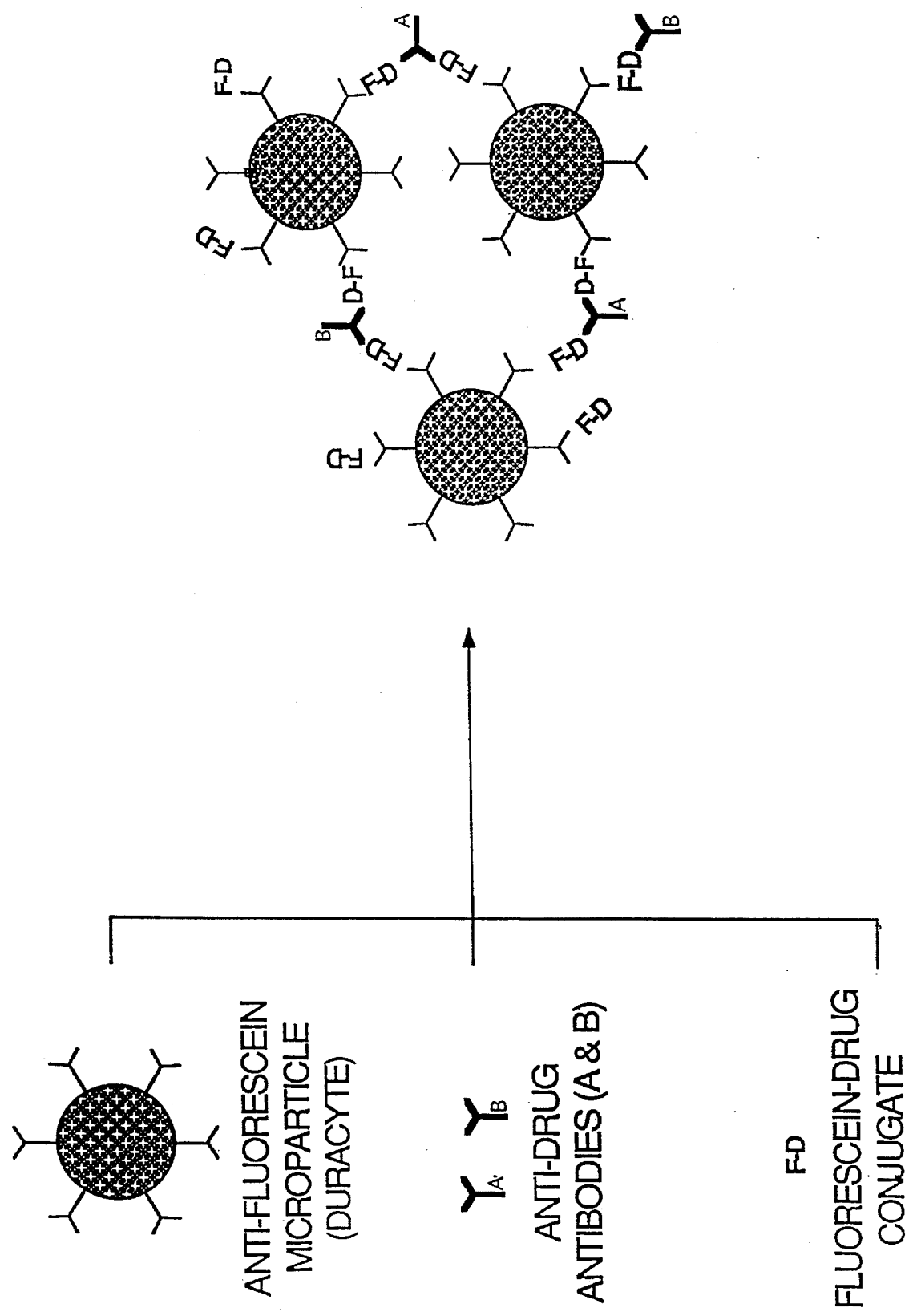
FIGS. 6–9 describe the dual antibody format.
Figure 7:
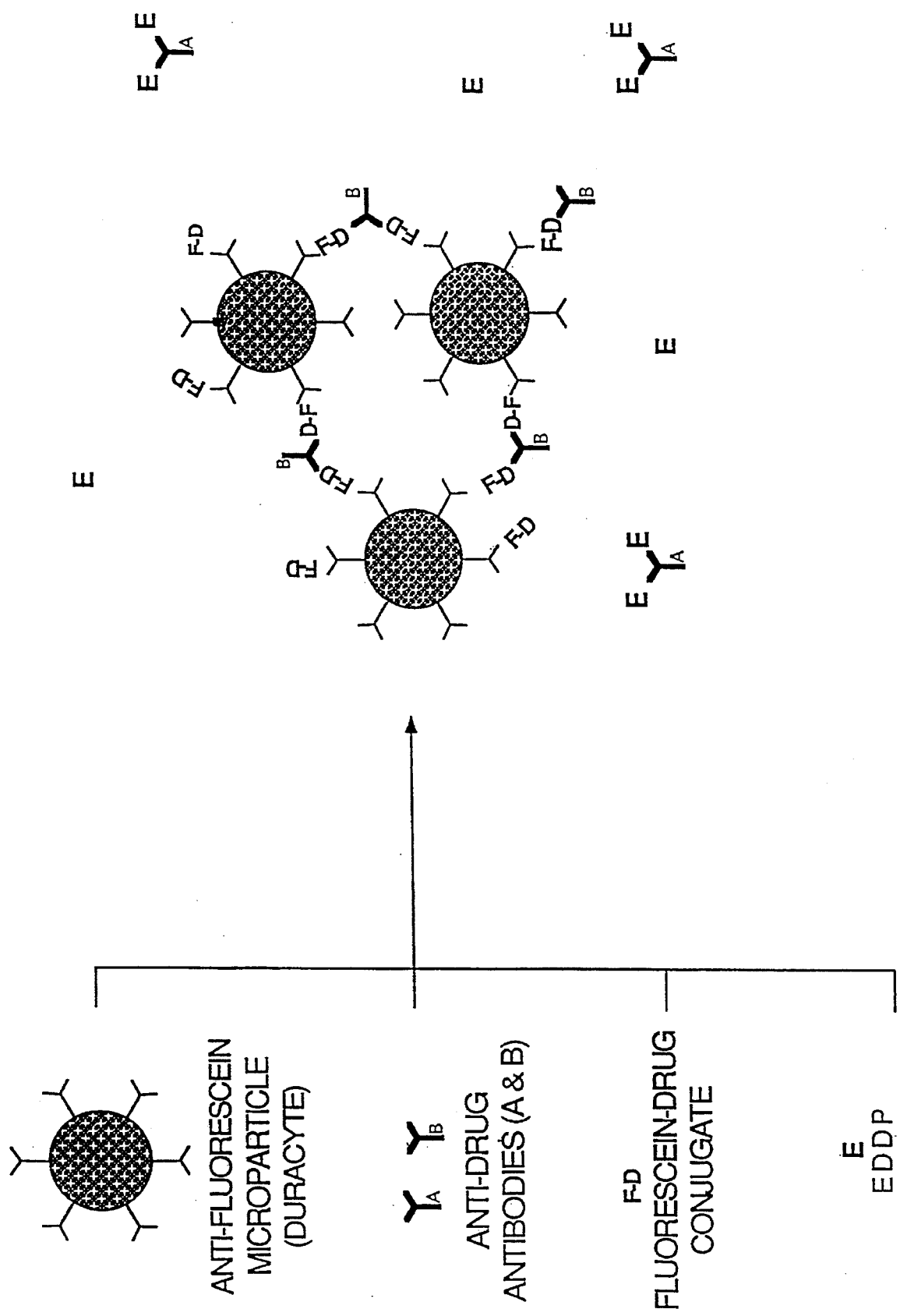
Figure 8:
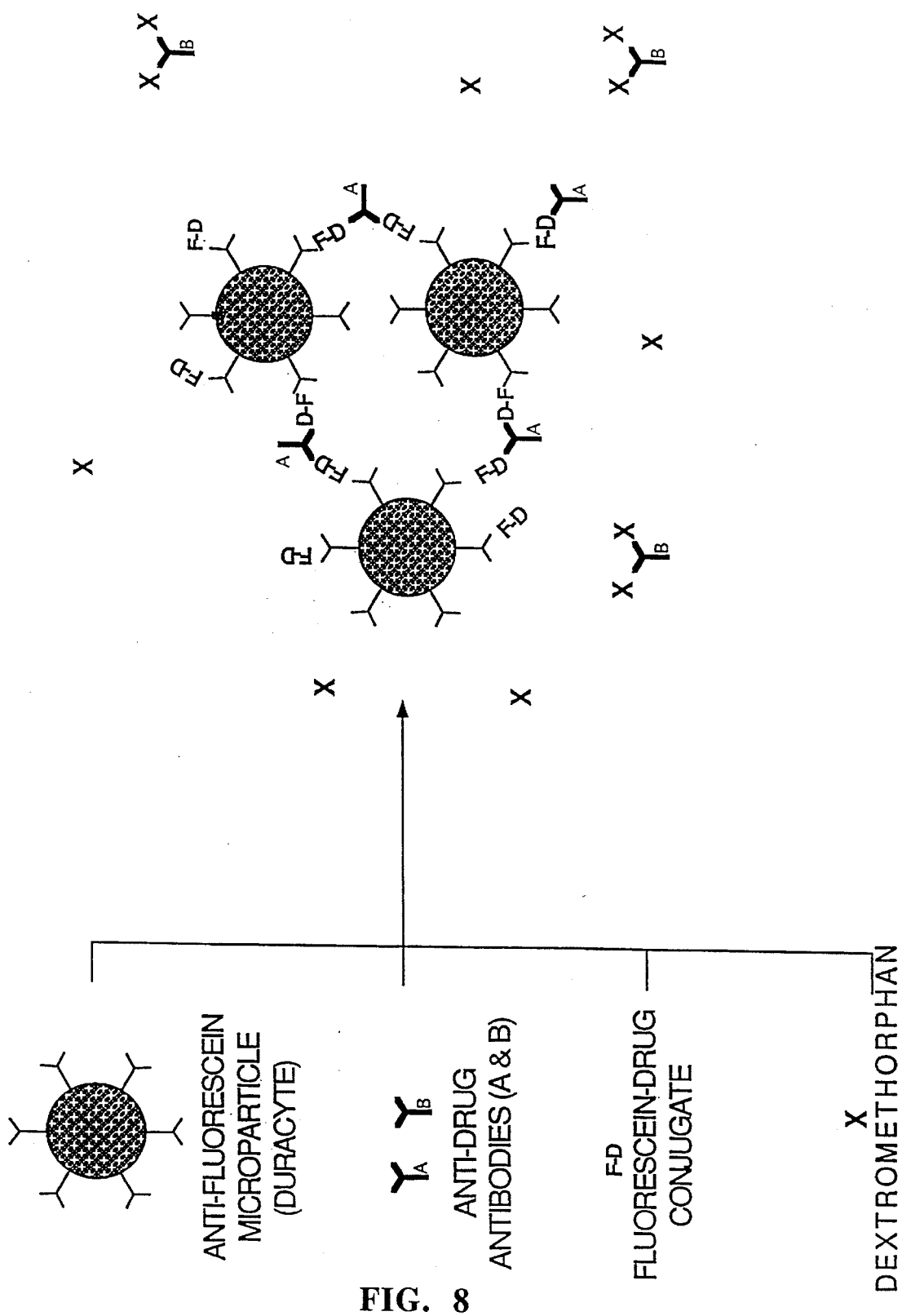
Figure 9:
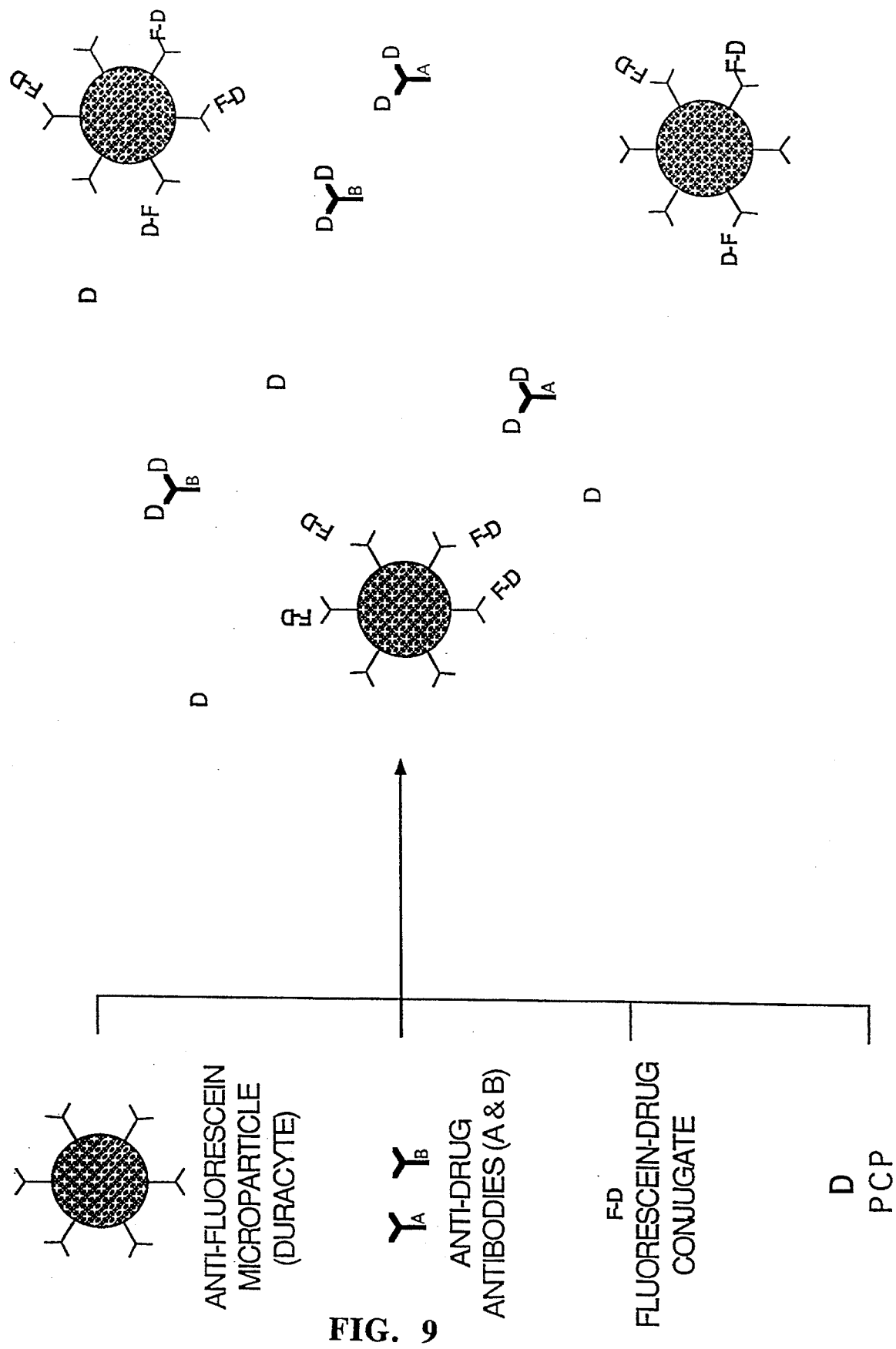

The preferred configuration for one format is as follows:

There are four major components in the system, the microparticle coated with an anti-hapten antibody (P-αH), the hapten-analyte conjugate (H-A), the anti-analyte antibody (αA) and the specimen containing the analyte (A). In the absence of the analyte (A), agglutinates of complexes of {(αH)(H-A)(αA)} are formed. This results in agglutination (see FIG. 1). In the presence of the analyte (A) however, all the antibodies (αA) are bound to the analyte (A), leaving no free antibody (αA) to bridge the complex formation (see FIG. 2). Thus no agglutination occurs. Therefore, a negative sample results in agglutination, a positive sample gives no or reduced agglutination. FIG. 5 shows the agglutinations in the cases of: negative, threshold, and positive reactions.

One configuration in the dual antibody format is as follows: There are three major components in the system, a particle, e.g., a microparticle coated with analyte or analyte-analog (P-A), the anti-analyte antibodies (αA and αB), and the specimen containing the analyte (A). In the absence of the analyte (A), agglutinates of complexes {(P-A)(αA)} or {(P-A)(αB)}, or {(P-A)(αA)(αB)} or combinations of the three are formed. The complexes result in agglutination. Additionally, the dual antibody format has the advantage of preserving assay integrity by adding at least two antibodies with different specificities for analyte (A). By doing so, either (αA) or (αB) can cross react with an interfering substance for which they have some cross reactivity to while the other antibody continues to bind the analyte (A) if present in the test sample or bind (M-A) if analyte (A) is not present in the test sample.

Another configuration in the dual antibody format is as follows:

There are four major components in the system, the microparticle coated with an anti-hapten antibody (P-αH), the hapten-analyte conjugate (H-A), the anti-analyte antibodies (αA and αB), and the specimen containing the analyte (A). In the absence of the analyte (A), agglutinates of complexes of {(αH)(H-A)(αA)} are formed. This results in agglutination (see FIG. 1). In the presence of the analyte (A) the dual antibody format has the advantage of preserving assay integrity by adding at least two antibodies with different specificities for analyte (A). By doing so, either (αA) or (αB) can cross react with an interfering substance for which they have some cross reactivity to while the other antibody continues to bind the analyte (A) if present in the test sample or bind (αH)(H-A) if analyte (A) is not present in the test sample. FIG. 5 shows the agglutinations in the cases of: negative, threshold, and positive reactions.

One skilled in the art would also realize that the hapten-anti-hapten pairing can be replaced with ligand-receptor pairings; biotin-avidin pairings; pairings of complementary nucleic acids; and any pairing that would allow for agglutination.

MULTI-ANALYTE ASSAY

One aspect of the invention can be conducted on a multi-chamber agglutination device. Each chamber is specific for detecting a specific analyte, and contains a reagent specific for that particular analyte. The device preferably allows the sample/reaction mixture to simultaneously flow into each chamber and to react within the chamber, but does not allow the reverse flow or intermixing of the reaction mixture in one chamber with that of the other chambers.

The test for a given analyte $(A_x)$ requires specific conjugate $(H-A_x)$ and anti-$A_x$ antibody $(\alpha A_x)$, and at least a second anti-$A_x$ antibody $(\alpha B_x)$ when utilizing the dual antibody format. The coated particle (P-αH) however, is common for all analytes in this test format, and becomes a generic reagent in the system.

For multi-analyte assay, one or both of the analyte-specific components $(H-A_x)$ or $(\alpha A_x)$ can be pre-packaged in respective chambers for each analyte in a manifold-chamber device. Additionally, when another anti-analyte antibody $(\alpha B_x)$ is used in the dual antibody format, the additional antibody with specificity for analyte $A_x$ can also be pre-packaged in respective chambers. The preferred devices are disclosed in U.S. patent applications Ser. No. 138,253, filed on Dec. 23, 1987, entitled "Agglutination Reaction Device" to Parsons, R. G., et al.; Ser. No. 614,762, filed Nov. 16, 1990, entitled "Improved Agglutination Reaction Device Utilizing Selectively Impregnated Material", to Forney, R. J., et al.; Ser. No. 614,895, filed Nov. 16, 1990, entitled "Improved Agglutination Reaction Device Utilizing Porous Absorbent Material" to Ropella, P. J., et al; and Ser. No. 614,817, filed Nov. 16, 1990,"Improved Agglutination Reaction Device Having Geometrically Modified Chambers", to Parsons, R. G. et al. These. applications are herein incorporated by reference.

One example of these multi-chamber devices is shown in FIGS. 3A and 3B, which show two views of a multi-channel device. Preferably, different hapten-analyte conjugate (H-A) is contained within each channel. In each chamber, the conjugates (H-A) bear the specific analytes to be detected in that particular chamber. In a competitive assay, the base of the chamber can be made of the any of the solid phase materials described above. The device contains means for introducing a portion of the sample into each chamber and mixing it with the conjugates to form a mixture and yet preventing the mixture from entering another chamber. Similarly, the device would also contains means for allowing the unbound reagents to be separated from the complex bound to the solid phase. For example, if washing is used as a separation step, the device similarly allows the wash solution to enter and exit each chamber carrying with it the unbound reagents, and yet does not allow the wash solution with the unbound reagents to enter another chamber. To achieve this latter end, the same means that separate the sample mixture in one chamber from the other may be used.

Alternatively, a simple microtiter well plate with anti-hapten antibodies bound to its wells could be used to carry out the competitive assay format, as exemplified in Example 13 below.

In the most preferred embodiment, an agglutination format is utilized for the multi-analyte assay. The H-A conjugates can be dissolved in an aqueous solution, and spotted onto the base of each of the channels and allowed to dry before the sample mixture is introduced, see e.g. Example 10 below. The mixture containing the specimen, the coated particle (P-αH), the $(\alpha A_x$'s), and $(\alpha B_x$'s) if utilizing the dual antibody format, are introduced to the sample loading zone. As a portion of the mixture flows into the individual channels, the specific conjugates become mixed to form complete reaction mixtures in each channel. The agglutination reaction does not start until the reaction mixture is completed by the combination of microparticles coated with antihapten antibodies, hapten-analyte conjugate, and anti-analyte antibody or antibodies. By placing different hapten-analyte conjugates (H-Ax, H-Ay, H-Az . . . ) in each channel, and using a cocktail of anti-analyte antibodies (αAx, αAy, αAz . . . ) and (αBx, αBy, αBz . . .) when the dual antibody format is utilized, mixed with the microparticles, distinct, simultaneous assays for analytes x, y, z, etc. will occur in each respective channel. Test results for different analytes will be manifested in the individual channels which contain the specific hapten-analyte conjugates.

Alternative versions of test configurations can be realized. All versions can be implemented as the panel test format, as well as the single test format.

Examples of the components of the assays including the dual antibody format are as follows:

A. The Analytes

The analyte includes low molecular weight substances, e.g., steroids such as testosterone, steriol, progesterone, corticosterone, aldosterone; thyroid hormones such as thyroxine and triiodothyronine; physiologically active peptides e.g. bradykinin, angiotensin, thyroid hormone-releasing hormone, and luteinizing hormone-releasing hormone; physiologically active amines such as epinephrine, norepinephrine, histamine, and serotonin; prostaglandin; relatively low molecular weight substances, e.g., insulin, glucagon, adrenocorticotropic hormone, and gastrin; and high molecular weight substances, e.g., human chorionic gonadotropin, growth hormone, human placental lactogen, immunoglobulin E, alpha-fetoprotein, hepatitis B antigen. The analyte can be a hapten, an antigen, or an antibody. Examples of antigens include antigens of micro-organisms such as human immunodeficiency virus (HIV) antigens, tumor-specific antigens, cell or tissue antigens, and serum antigens. The analyte is preferably small molecules such as therapeutic drugs, drugs of abuse, and toxins.

B. The Particles and Methods for Coating Them

The particles are preferably microparticles that are visually detectable, colored microparticles which enable a direct visual readout of the presence or concentration of the analyte in the test sample without the need for using additional signal producing reagents. Materials for use as such particles include colloidal metals, such as gold and dyed particles as disclosed in U.S. Pat. Nos. 4,313,734 and 4,373,932. The preparation and use of non-metallic colloids, such as colloidal selenium particles, are disclosed in co-owned and copending U.S. patent application Ser. No. 072,084, filed Jul. 9, 1987, which is incorporated by reference herein. Organic polymer latex particles can also be used. They are disclosed in co-owned and copending U.S. patent application Ser. No. 248,858, filed Sep. 23, 1988, which is incorporated by reference herein. Other particles of natural or organic polymers can also be used. Other preferred particles are cells which can agglutinate, e.g., erythrocytes, preferably fixed erythrocytes such as Duracyte™ cells (Abbott Laboratories, North Chicago, Ill.). An example of how the erythrocytes can be fixed (i.e. stabilized) is shown in *J. Immunology*, 100 (3):641 (1988). The selection of a particular particle is not critical, so long as the particle is capable of agglutination and such agglutination can be visually detected.

Anti-hapten antibody is attached to the particle via covalent binding and/or adsorption using known methods. For example, particles such as latex particles can be passively coated with the antibodies (Hadfield, et al., *J. Imm. Methods*, supra) The method for coating antibodies onto selenium particles disclosed in the Examples below can also be used to coat other metal particles, such as gold particles. For an alternative method, see e.g. the method disclosed in U.S. Pat. No. 5,075,100 to Seno, for preparing iron colloid-labeled antibodies.

C. The Haptens and Anti-Hapten Antibodies

The hapten can be any small molecule capable of eliciting immune responses in laboratory animals, usually when conjugated to a protein. Preferably, the hapten only has one antigenic site. Examples of these haptens are fluorescein, rhodamine, biotin, and dinitrophenyl groups. Anti-hapten antibodies can be produced with methods known in the art, and the antibodies can be polyclonal or monoclonal antibodies. Polyclonal antibodies can be produced for example, by injecting a host animal such as rabbit, rat, goat, mouse etc. with the hapten. Before injection, the hapten can be first conjugated with carriers such as keyhole limpet hemocyanin or bovine serum albumin. Monoclonal antibodies can be produced, e.g. according to the method disclosed in Kohler Mulstein, *Nature*, 256:495–497 (1975) . The antibodies can also be recombinant monoclonal antibodies, for example, produced according to the methods disclosed in Reading U.S. Pat. No. 4,474,893, or Cabilly et al., U.S. Pat. No. 4,816,567. Within the scope of antibodies are also antibody fragments such as Fab, F(ab')2, and Fv fragments. Such fragments can be produced by known techniques.

D. The Hapten-Analyte Conjugates

The hapten-analyte conjugates, such as fluorescein-analyte conjugates are commercially available for the commonly assayed analytes, for example they are used as the tracers in Abbott Laboratories' TDX's FPIA (commercially available from Abbott Laboratories, Abbott Park, Ill.). The hapten-analyte conjugates can also be produced according to methods known in the art, such as disclosed in U.S. Pat. No. 4,668,640 to Wang et al.

Figure 2:
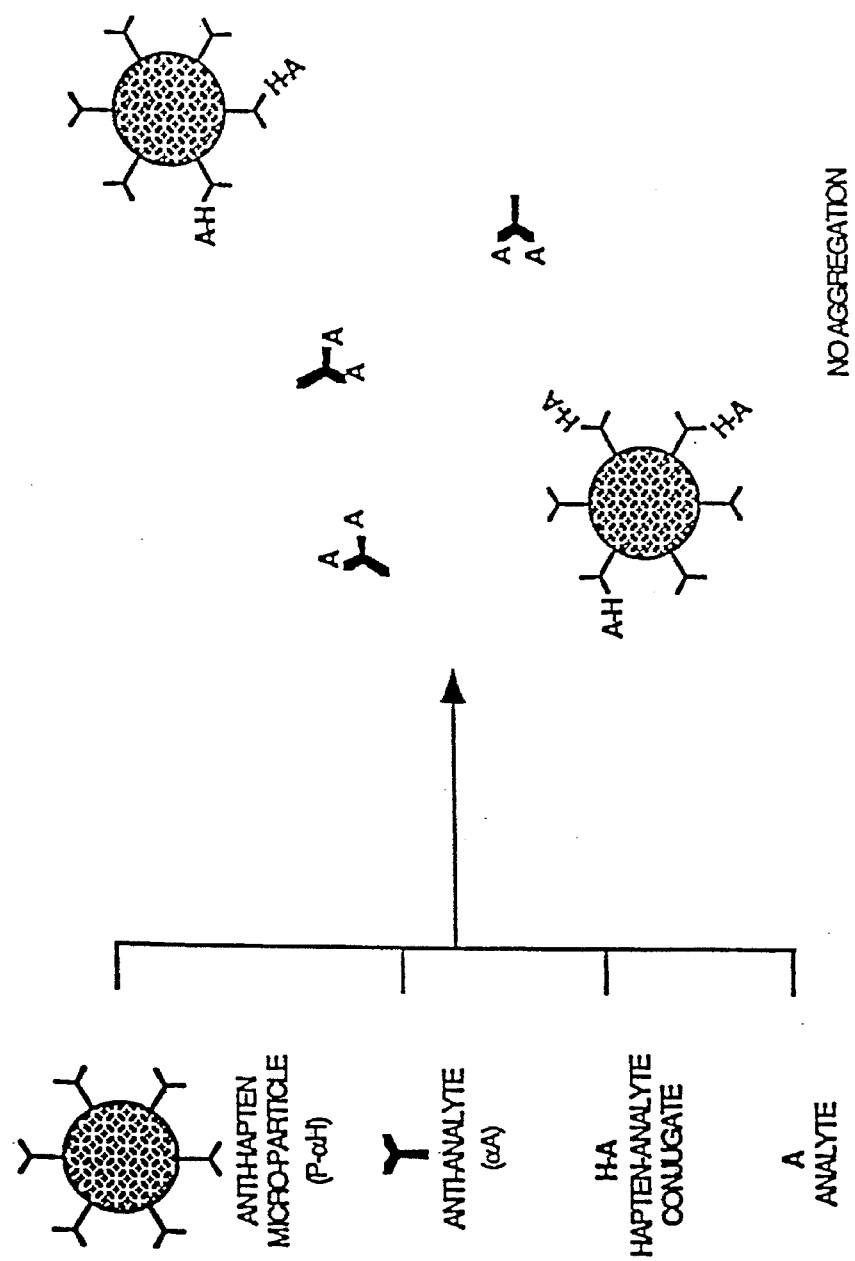
FIG. 2 illustrates the inhibition of agglutination in the presence of analytes.

The following are examples of assay formats that can be used for any analyte:

a. Competitive Assay (FIGS. 1 & 2). Members of the immunoreaction consist of the microparticle coated with anti-hapten antibody, the hapten-analyte conjugate, the anti-analyte antibody or antibodies and specimen.

In the test, the analyte in the specimen competes with the hapten-analyte conjugate for the anti-analyte antibody or antibodies. The more analytes that are present in the specimen, the less the anti-analyte antibodies will be available for agglutination; and vice versa. Thus the observed agglutination is inversely proportional to the analyte concentration in the specimen.

b. Direct Sandwich Assay for antibody.

Figure 4:
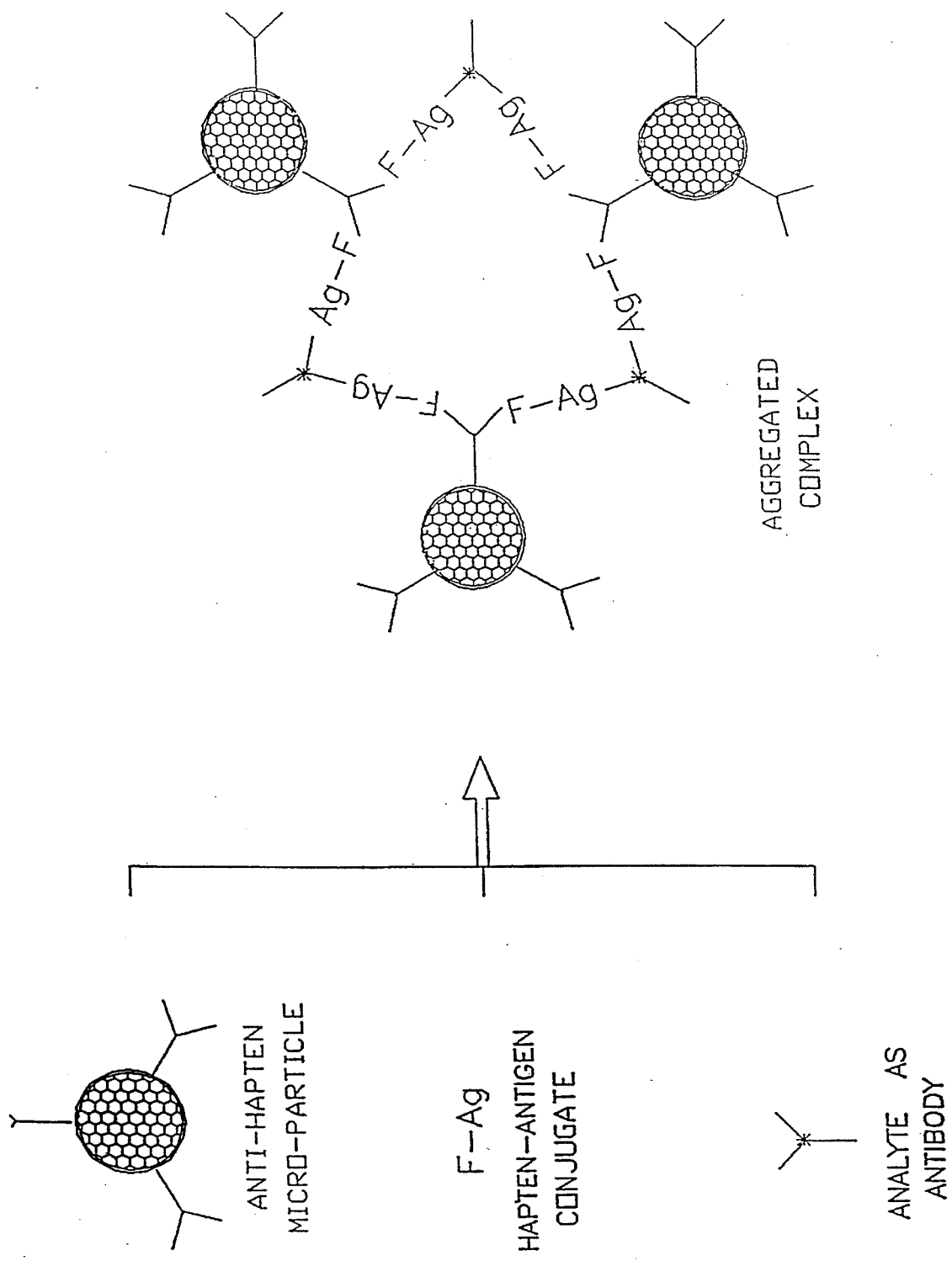
FIG. 4 illustrates a sandwich assay format for the antibody test.

Similarly, the configuration can also be arranged to test for antibodies (Ab). Thus, the antibodies of interest become the analytes. The sample is mixed with the anti-hapten antibody coated microparticles (P-vH), and conjugates of the haptens with antigens for which the antibodies of interest are specific for (H-Ag). The concentration of antibodies in the sample is directly proportional to the amount of agglutination caused by the formation of complexes of {(P-αH)(H-Ag)(Ab)} (as shown in FIG. 4).

E. Dyed Particles and The Dyeing Methods

The present invention also presents dyed erythrocytes, preferably dyed fixed erythrocytes, to enhance visualization of the agglutination process. U.S. Pat. No. 4,745,075, to Hadfield et al., in column 3, has suggested dyeing erythrocytes that are used agglutination assays. The patent indicated that the erythrocytes may be prepared or dyed according to standard methods, see e.g. U.S. Pat. No. 4,419,453 and German Patent Application DT-3000-483, and that particularly suitable colors include red, yellow, blue, green, black, cyan, magenta, and white.

The current invention presents erythrocytes which can be dyed, for example, red, green or blue. The dyed erythrocytes, preferably fixed erythrocytes such as the commercially available Duracyte™ cells, can be coated with antibodies and the antibodies still maintain their abilities to bind their antigens and cause agglutination of the dyed erythrocytes. Dyed particles can be used at lower concentrations than their non-dyed counterparts with comparable performance. Preferably, the dyes firmly adhere to the cells and do not leach into the surrounding assay solution. The preferred dyes for cells such as fixed erythrocytes are: Cibachrome Blue 3GA (Sigma Chemical Co., St. Louis, Mo.); the Reactive Color Series from Sigma Chemical Co., such as Reactive Red, Reactive Green, Reactive Yellow, etc.; diazonium dyes (such as Fast Black K, Fast Blue B from Sigma Chemical Co., St. Louis, Mo.); and organic dyes with Iodoacetamide or maleimide coupling chemistry (e.g. Rhodamine iodoacetamide, Rhodamine maleimide, Eosine iodoacetamide, Eosine maleimide, Tetramethylrhodamine maleimide, and Tetramethylrhodamine iodoacetamide). In the case of fixed erythrocytes, an important feature of the above listed dyes is that they couple to the erythrocytes via functional groups other than amino groups, since the erythrocytes have no or very few free amino groups available for binding dye. The most preferred dyes are those which covalently bind to the erythrocytes, preferably fixed erythrocytes. The intensities of the colors of the different particles are preferably balanced to achieve good differentiation between agglutination and lack thereof.

The dyed particles can be used in the above agglutination reactions where two or more populations of particles (of different colors) can be mixed to perform multiple assays. The different colored particles are preferably present in about equal amounts. Reactions with either of the populations of particles cause an overall change in the color of the solution which can be easily visualized. In the multi-analyte assay format using generic anti-hapten particles, other colored particles can be used, for example, differently colored latex and plastic particles. This greatly enhances one's ability to read these tests and allows for multiple tests to be run simultaneously. Thus, the invention poses an advantage over prior art where each individual assay and control are run separately, incurring extra time and labor.

EXAMPLES

Example 1

Staining of Fixed Human Erythrocytes with Coomassie Brilliant Blue R-250

Fixed human erythrocytes (Duracyte™, Abbott Laboratories, supra) were suspended in 0.1M citrate buffer, pH 3.0 at a final concentration of 5% (v/v). Coomassie Brilliant Blue R-250 dye (Biorad Labs., Richmond, Calif.) was added to a final concentration of 0.5% (w/v) and the cells were allowed to incubate at room temperature for 1.5 hours. Finally the cells were alternately centrifuged (1000×G, 1 min) and washed with phosphate buffered saline (PBS, 10 mM sodium phosphate and 0.15M NaCl, pH 7.4) until the supernatant had very little residual color. The resultant suspension of cells had a dark purple color.

Example 2

Staining of Fixed Human Erythrocytes with Cibacron Blue 3GA

A 10% suspension of Duracyte™ cells was prepared in 50 mM NaOH. Cibacron Blue 3CA (Sigma Chemical Co., St. Louis, Mo.) was added to the suspension to a final concentration of 50 mg/ml. The suspension was allowed to mix at room temperature for 1.5 hours. The cells were similarly centrifuged and washed as in Example 1. The resultant cell suspension had a dark blue color.

Example 3

Staining of Fixed Human Erythrocytes with Cibacron Red 2

A 10% suspension of Duracyte™ cells was stained red using the procedure described in Example 2 and Reactive Red 2 (Sigma Chemical Co., St. Louis, Mo.). The resultant cell suspension had a red color.

Example 4

Coating of Fixed Human Erythrocytes with Anti-fluorescein

A 10% (v/v) suspension of Duracyte™ cells were coated with affinity-purified rabbit anti-fluorescein at a concentration of 100 µg/mL in the presence of 0.05% (w/v) chromic chloride in 0.1M sodium acetate buffer at pH 4.0. The suspension was incubated at 30° C. for 1 hour with occasional mixing via inverting the reaction test tube. After centrifugation (1000×G, 1 min), the cells were washed two times with 8X Volume of PBS and then incubated with 1% (w/v) human serum albumin (Sigma Chemical Co., St. Louis, Mo.) in 25 mM Tris/HCl buffer (pH 8.0) at room temperature for 30 minutes. The cells were finally resuspended in PBS (see Example 1) to a final cell concentration of 10% (v/v).

Example 5

Coating of Colloidal Selenium with Anti-fluorescein

About 57 mL of stock selenium colloid ($OD_{550}$ 12.3) (prepared according to the method disclosed in U.S. patent application Ser. No. 072,084, supra) was centrifuged at 750×G for 25 min. The soft pellet was suspended in 20 mL of Milli-Q water (Millipore Corp., Bedford, Mass.). The centrifugation and resuspension was repeated twice. The pH of 400 ml Milli-Q water was carefully adjusted with 0.2% sodium carbonate to 7.8. About 8.7 mL (OD 550=688) of the selenium was added to the pH 7.8 solution. Then 0.5 mg of protein-A purified rabbit-anti-fluorescein IgG was added to the selenium suspension. This was gently stirred at 2°–8° C. overnight. Bovine serum albumin (BSA, Sigma Chemical Co., St. Louis, Mo.) was added to the suspension to a concentration of 0.5%. Stirring was continued for another 2 hours. The mixture was washed as described above via centrifugation. After the last centrifugation, the pellet was suspended in 0.1% BSA, 5 mM HEPES (N-[2-hydroxyethyl]piperazine-N'-[2-ethanesulfonic acid], Sigma Chemical Co., St. Louis, Mo.), pH 7.8 to give an $OD_{550}$ of 2.0 when 15 µL was diluted into 1 mL of water. This was stored at 2°–8° C.

Example 6

Coating of Colloidal Polypyrrole with Antifluorescein

Stock polypyrrole (PP) at 1 mL, ~350 $OD_{800}$/ml was washed 3 times with water (1 mL) via centrifugation at 1000×G, 5 min each (International Equipment Co., Needham Height, Mass.). About 200–300 µl of the washed PP was mixed with 0.5 ml of 250 mM MES (2-[N-morpholino]ethanesulfonic acid, Sigma Chemical Co., St. Louis, Mo.) pH 7.0 and 4.5 mL water and 10–250 µg of protein-A purified rabbit anti-fluorescein IgG for 10 min. BSA was added to the mixture to a concentration of 0.05%. The suspension was mixed for another 10 min. The preparation was then washed 3 times with (1 mL) 0.5% BSA, 35 mM MES at pH 7.0. The mixture was finally suspended in 50 µl of the same buffer.

Example 7

Fixed Human Erythrocytes anti-fluorescein Assay for Cocaine Metabolites (Benzoylecognine)

One mL of anti-fluorescein-coated Duracyte™ cells (see Example 4) was resuspended in 3 ml Duracyte buffer (0.067M sodium phosphate at pH 8.0, 0.75M NaCl, 20 mM EDTA (ethylenediamine tetraacetic acid, Sigma Chemical Co., St. Louis, Mo.), 1.5% fetal calf serum, 6% Ampholyte (Pharmacia LKB Biotech., Piscataway, N.J.) and 0.1% sodium azide). For this assay, 25 µl of the above anti-fluorescein Duracyte™ cells, 5 µl of sheep anti-cocaine antisera, 10 µl of the urine specimen and 5 µl of a diluted fluorescein-cocaine conjugates (TDx cocaine tracer diluted at two-fold with 0.15M NaCl; The tracer was obtained from TDx Cocaine Metabolites Kit, commercially available from Abbott Laboratories, North Chicago, Ill.) were mixed, via repeated aspirating and dispensing, and then added to a laminated test card (similar to that disclosed in Example 1 of pending U.S. application Ser. No. 07/614,817, supra, except that each card used herein contained ten reaction channels). Within 5–10 min, the viewing areas of the test cards were visually examined for agglutination patterns indicative of positive or negative results. A granular agglutination pattern in the viewing zone indicated the absence of cocaine (Benzoylecognine) in the samples (negative result). A smooth pattern without any agglutination was found when samples with Benzoylecognine were used (positive result). Twenty known benzoylecognine-positive samples and 18 negative samples were tested. All positive samples gave positive results and all negative samples gave negative results.

Tests for opiates, cannabinoids, amphetamine and phencyclidine were analogously configured. Known positive and negative samples for each of the analytes all give the corresponding positive and negative results respectively.

Example 8

Colloidal Selenium anti-fluorescein Assay for Phencyclidine

Phencyclidine-fluorescein conjugate (PCP tracer from TDx PCP Reagent Kit, Abbott Laboratories, supra) was mixed with a stock preparation of anti-fluorescein-coated selenium (see Example 5) at a concentration of 0.04% (%). Thirty µl of the mixture was aliquoted into each of 4 test tubes. Five µl of urine samples containing 0, 25, 60, and 120 ng/mL phencyclidine were added to each of the test tubes. Then 5 µl of anti-phencyclidine antibody ($TD_x$ PCP antisera from $TD_x$ PCP Reagent Kit, Abbott Laboratories, supra) was added. After ~8 min at room temperature, 1 ml of water was added to each of the test tubes. The mixtures were vortexed and measured for optical density at 550 nm (nanometer). The results were:

| Phencyclidine Concentration (ng/mL) | $OD_{550}$ |
|---|---|
| 0 | .207 |
| 25 | .515 |
| 60 | .758 |
| 120 | .823 |

Tests for opiates, cannabinoids, cocaine and Thyroxine (T4) were analogously configured except that serum instead of urine samples were used in the case of T4. The results all showed increased $OD_{550}$ with increasing concentration of analytes.

Example 9

Polypyrrole-anti-fluorescein Assay for Thyroxine

In each of 2 test tubes, 7 µl of anti-fluorescein-coated polypyrrole (see Example 6) and 2 µl of thyroxine standards containing 0 µg/mL and 0.24 µg/ml in serum, respectively, and 1.5 ul of the TDx fluorescein-thyroxine tracer and 10 µl of anti-thyroxine antisera from TDx Thyroxine Kit, Abbott Laboratories, supra, were mixed. After 10 min incubation at room temperature, the reaction mixtures were quenched with 1 ml of water. Optical density at 800 nm were measured for both mixtures. The results were:

| Thyroxine Concentration µg/ml | $OD_{800}$ |
|---|---|
| 0 | 1.52 |
| 0.25 | 3.73 |

Example 10

Panel Test for Abused Drugs using Antifluorescein-coated Fixed Human Erythrocytes An aliquot (1 µL) of the TDx Fluorescein-drug tracer solution from each of the TDx assay kits for Cocaine Metabolites, Opiates, and PCP (Abbott Laboratories, supra) was placed and dried in a different channel of a laminated reaction card (The reaction card is described in Example 7). These reagent spots were positioned in the narrow, straight portions of the reaction channels. An antisera cocktail was made by mixing 20 µl from each of the three antisera solutions (Antisera solutions from TDx reagent kits) from each of the same three assay kits along with 16 µl of a 10% suspension of anti-fluorescein coated Blue Duracyte™ cells (Examples 2 and 4), and 64 µl Duracyte Buffer (Example 7). This cocktail (140 µl) was mixed with 40 µl of a normal (drug free) urine sample and 45 µl aliquots of the resultant solution were added to the laminated reaction cards and from there the solution flowed (through capillary action) into the channels having each of the three respective tracers. Within 5 minutes strong agglutination patterns were visible in each of the three channels. This experiment was repeated using samples which contained various concentrations of either Benzoylecognine, morphine, or PCP and the results are presented in the Table below:

|  | REACTION NUMBER | | | | | | | |
|---|---|---|---|---|---|---|---|---|
|  | 1 | 2 | 3 | 4 | 5 | 6 | 7 | 8 |
| DRUG | DRUG IN SAMPLE (ng/mL) | | | | | | | |
| Benzoyl | 0 | 1670 | 0 | 0 | 1670 | 1670 | 0 | 1670 |
| Morph | 0 | 0 | 330 | 0 | 330 | 0 | 330 | 330 |
| PCP | 0 | 0 | 0 | 167 | 0 | 167 | 167 | 167 |
| TRACER | AGGLUTINATION IN CHANNELS | | | | | | | |
| Cocaine | + | − | + | + | − | − | + | − |
| Opiate | + | + | − | + | − | + | − | − |
| PCP | + | + | + | − | + | − | − | − |

In every case when a given drug (either Benzoylecognine, Morphine, or PCP) was present in the sample, the agglutination reaction was inhibited in the reaction card channel that had the Tracer corresponding to that drug. The presence of a given drug did not have any effect on the agglutination reactions in the channels that contained tracers for the other drugs.

Example 11

Coating of Fixed Human Erythrocytes with Hepatitis B Surface Antigen (HBsAg)

Cibacron Blue 3GA-stained fixed human erythrocytes (see Example 2) were coated with monoclonal anti-HBsAg at a final concentration of 120 µg/ml using the procedure described in Example 4, The coated cells were suspended in Duracyte buffer (Example 7) at a final concentration of 10% (v/v). These cells (25 µL) were mixed with 25 µL of either serum containing 12 ng/ml HBsAg or serum without any HBsAg (25 µL) and added to the channels of laminated reaction cards (Example 7). The cells mixed with serum containing HBsAg formed strong agglutinates whereas the cells mixed with serum without HBsAg did not agglutinate.

Example 12

Specific Color-coded Assay for HBsAa

An equal volume of the red stained (uncoated) Duracyte™ cells (Example 3) were mixed with the blue stained (anti-HBsAg coated) Duracyte™ cells (Example 11 ). The resulting suspension was a dark gray or black color. This mixed Duracyte™ cell suspension was mixed with serum samples containing either 25 ng/ml or zero HBsAg as described in Example 11. In the sample containing HBsAg, the blue Duracytes™ cells agglutinated and were clearly visible against a pink background (unagglutinated red Duracyte™ cells). In the sample without HBsAg, the gray-colored suspension remained as uniform color and did not show signs of agglutination.

Example 13

Affinity purified anti-fluorescein is diluted with buffer (10 mM Tris-HCl, pH 9.0, 150 mM NaCl) to a final concentration of 50 µg/mL. 100 µL aliquots of this material is incubated in each of the wells of a 96 well microtiter plate for 12 hr at 37° C. The non-bound anti-fluorescein is next aspirated from the wells, and the wells are washed five times with 100 µL amounts of PBS containing 0.1% BSA. At this point the microtiter plate wells contain an adsorbed, non-soluble coating of anti-fluorescein (coated microtiter plate).

Mixtures (100 µL) of urine samples containing known amounts of Phencyclidine (PCP), a PCP-fluorescein conjugate, and an alkaline phosphatase labeled anti-PCP antibody, are added to the wells, such that the first well contains no free PCP, the second well contains 25 ng/mL PCP and the third well contains 250 ng/mL of PCP. The microtiter plate is incubated for 1 hour at 37° C., and the contents of each well are aspirated and the wells are washed five times with 100 µL of PBS containing 0.1% BSA. Alkaline phosphatase substrate reagent (Sigma 104 Phosphatase Substrate, Sigma Chemical Co., St. Louis, Mo.) is added in 100 µL amounts to each of the wells, and after 10 minutes incubation, a yellow color is observed to be developing in the well which did not contain PCP, whereas the wells with increasing concentrations of PCP have decreasing amounts of color. In this assay, the amount of color developed is inversely proportional to the amount of PCP in the sample.

Analogous assays for other drugs (opiates, amphetamine, etc.) are performed in other wells of the same coated microtiter plate by adding samples containing mixtures of specific fluorescein conjugates of those drugs and their respective enzyme-labeled antibody pairs, in the place of the PCP-fluorescein and the enzyme-labeled anti-PCP used in the example above.

Example 14

Aliquots (1.5 µL) of fluorescein-drug tracer solutions for amphetamines, cannabinoids, cocaine, opiates, and PCP (from the respective TDx assay kits available from Abbott Laboratories, supra) are placed and dried in channels 2–6 of the laminated reaction card (FIGS. 3A and 3B show two views of the card). For a negative control, another 1.5 µL of Fluorescein labeled BSA (Sigma Chemicals, St. Louis, Mo.) diluted to 0.5 mg/mL in PBS is added to channel 1 of each card. For a positive control, channel 7 of each of the card is left without any dried reagents. An antisera cocktail with antifluorescein coated Duracyte cells is prepared as described in Example 10, however, additional antisera directed against cannabinoids and amphetamines are also added. A 200 µL sample of this antibody cocktail is mixed with 20 µL of normal (drug-free) human urine, and then introduced into the center of the reaction card. The liquid simultaneously flows into each of the channels and mixes with the reagents dried therein. After 5 minutes, the appearance of aggregated cells is clearly visible in Channels 1–6. Channel 1 represents a negative reaction reference and it will show a reaction analagous to the negative assays, independent of whether negative or positive samples are run. Channels 2–6 provide the individual reactions for each of the 5 drugs (amphetamines, cannabinoids, cocaine, opiates, and PCP) corresponding to the individual drug tracers placed in the channels. The Duracyte cells in channel 7 do not aggregate, since no tracer or other reagents are present in this channel, and therefore it provides a positive reaction reference.

Example 15

Sixteen test samples were tested to determine and evaluate antibodies which would prevent cross-reactivity thereby giving adequate results. Sheep polyclonal antibody for PCP was used as the anti-analyte antibody. Five different monoclonals (Mab) were tested for their ability to bind the structurally related substance 2-ethylidene-1,5-dimethyl-3,3-diphenylpyrrolidine (EDDP). Particles used were Duracyte™ and the assay run on Advisor® (Abbott Laboratories) test kits. The samples contained EDDP without PCP present. The reaction strengths of the assays were determined visually using a semi-quantitative scoring system where 0.5=no agglutination, and 4.0=very strong agglutination. Assays with intermediate reaction strengths were given numerical scores between 0.5 and 4 which reflected the relative intensity of the reactions.

| | AGGLUTINATION IN CHANNELS | | | | | |
|---|---|---|---|---|---|---|
| Sample | Poly | Mab#1 | Mab#2 | Mab#3 | Mab#4 | Mab#5 |
| 1 | 0.5 | 2.0 | 4.0 | 1.5 | 3.5 | 1.5 |
| 2 | 1.0 | 2.0 | 4.0 | 1.5 | 4.0 | 1.0 |
| 3 | 1.0 | 1.0 | 4.0 | 1.0 | 4.0 | 2.0 |
| 4 | 1.5 | 2.0 | 4.0 | 1.5 | 3.5 | 1.0 |
| 5 | 0.5 | 1.5 | 4.0 | 1.0 | 3.5 | 1.0 |
| 6 | 2.0 | 1.5 | 4.0 | 1.0 | 3.5 | 1.0 |
| 7 | 2.0 | 1.5 | 4.0 | 1.5 | 3.5 | 0.5 |
| 8 | 2.0 | 1.0 | 4.0 | 1.5 | 3.5 | 0.5 |
| 9 | 0.5 | 2.0 | 4.0 | 1.5 | 3.5 | 0.5 |
| 10 | 1.5 | 1.5 | 3.5 | 1.5 | 3.5 | 2.0 |
| 11 | 0.5 | 1.5 | 4.0 | 1.5 | 3.5 | 2.0 |
| 12 | 2.0 | 1.5 | 4.0 | 2.0 | 4.0 | 1.5 |
| 13 | 2.0 | 1.5 | 4.0 | 1.5 | 3.5 | 1.5 |
| 14 | 2.0 | 2.0 | 4.0 | 2.5 | 4.0 | 2.0 |
| 15 | 2.0 | 0.5 | 4.0 | 2.5 | 4.0 | 2.0 |
| 16 | 3.0 | 1.5 | 4.0 | 1.5 | 3.5 | 1.5 |

These results showed the tendency of Monoclonal antibodies #2 and #4 not to bind structurally related substance EDDP and allow complex formation with the anti-fluorescein coated particles and the PCP-fluorescein conjugate.

Example 16

These five test samples were tested with samples containing a different structurally related substance, 2-ethyl-5-methyl- 3,3-diphenylpyrroline (EMDP), without PCP. The same antibodies were used as in Example 15. The reaction strengths of the assays were determined visually using a semi-quantitative scoring system where 0.5=no agglutination, and 4.0=very strong agglutination. Assays with intermediate reaction strengths were given numerical scores between 0.5 and 4 which reflected the relative intensity of the reactions.

| Antibody | Negative | 10 ug/ml | 100 ug/ml |
| --- | --- | --- | --- |
| Poly | 4.0 | 4.0 | 3.5 |
| Mab #1 | 2.0 | 2.0 | 2.0 |
| Mab#2 | 4.0 | 4.0 | 4.0 |
| Mab #3 | 2.0 | 2.0 | 2.0 |
| Mab #4 | 3.5 | 3.5 | 3.5 |
| Mab #5 | 2.5 | 1.5 | 1.5 |

Despite a different structurally related substance being used, Mab #2 and #4 do not bind the substance thereby permitting complex formation and agglutination.

Example 17

Some of the same antibodies in Example 16 were tested for their ability to analyze two different levels of PCP as well as their specificity to EDDP and dextromethorphan in the absence of PCP. The monoclonal antibodies were then individually mixed 50:50 with the polyclonal and tested against the same analyte and interfering substances. The reaction strengths of the assays were determined visually using a semi-quantitative scoring system where 0.5=no agglutination, and 4.0=very strong agglutination. Assays with intermediate reaction strengths were given numerical scores between 0.5 and 4 which reflected the relative intensity of the reactions.

| Antibody | 0.5PCP (12.5 ng/ml) | 1.5PCP (37.5 ng/ml) | Dextromethorphan (100 μg/ml) | EDDP (100 μg/ml) |
| --- | --- | --- | --- | --- |
| POLY | 3.5 | 0.5 | 3.5 | 0.5 |
| Mab#2 | 1.8 | 0.5 | 0.5 | 2.0 |
| Mab#3 | 1.8 | 0.5 | 1.5 | 1.5 |
| Mab#4 | 2.3 | 0.8 | 2.5 | 2.5 |
| Mab#5 | 2.3 | 2.0 | 2.5 | 2.5 |
| POLY/Mab#2 | 3.5 | 0.8 | 3.5 | 3.5 |
| POLY/Mab#3 | 1.0 | 0.5 | 3.5 | 1.0 |
| POLY/Mab#4 | 2.5 | 0.5 | 2.5 | 2.5 |
| POLY/Mab#5 | 1.5 | 0.5 | 2.0 | 0.5 |

The results showed that a blend of polyclonal and particular monoclonals gave the best results in detecting analyte both in the presence and absence of interfering substances.

The assay threshold for samples is set at 25 ng/ml of PCP. Accordingly, samples listed in the 0.5 PCP are at half the PCP threshold and therefore should show agglutination. Conversely, samples at the 1.5 PCP concentration should show little or no agglutination.

All publications and patent applications mentioned in this Specification are herein incorporated by reference to the same extent as if each of them had been individually indicated to be incorporated by reference.

Although the foregoing invention has been described in some detail by way of illustration and example for purposes of clarity and understanding, it will be obvious that various modifications and changes which are within the skill of those skilled in the art are considered to fall within the scope of the appended claims. Future technological advancements which allows for obvious changes in the basic invention herein are also within the claims.

We claim:

1. An immunoassay method for detecting the presence or measuring the amount of an analyte (A) in a test sample comprising:

a) exposing the test sample to a particle-analyte (P-A) and a common antibody pool to form a reaction mixture, wherein said particle-analyte (P-A) comprises a particle (P) attached to analyte (A) and said common antibody pool comprises (1) at least two antisera, one of said at least two antisera containing an antibody αA, the other of said at least two antisera containing an antibody αB, or (2) at least one antisera and at least one monoclonal antibody, said at least one antisera containing an antibody αA and said monoclonal antibody being antibody αB, or (3) at least two monoclonal antibodies, one of said at least two monoclonal antibodies being antibody αA, the other of said at least two monoclonal antibodies being antibody αB, wherein antibody αA and antibody αB have different binding specificities for analyte (A), one of which antibodies αA or αB is also able to cross-react with other substances that are structurally related to analyte (A), while the other antibody cannot cross-react with said substances;

b) allowing the formation of complexes including (P-A)(αA), or (P-A)(αB), or (P-A)(αB)(αA), or combinations of the three; and c) detecting the presence or measuring the amount of any of (P-A)(αA), or (P-A)(αB), or (P-A)(αB)(αA), or combinations of the three in the absence of analyte (A); or the absence of (P-A)(αA), or (P-A)(αB), and (P-A)(αB)(αA) in the presence of analyte (A).

2. The immunoassay method of claim 1, wherein said particle is selected from the group consisting of: cells, polymeric microparticles, selenium microparticles, iron microparticles, and gold microparticles.

3. The immunoassay of claim 1, wherein said particle has a color providing detection of the complexes.

4. The immunoassay method of claim 2, wherein said cells are dyed erythrocytes.

5. An immunoassay method for detecting the presence or measuring the amount of an analyte (A) in a test sample comprising:

a) exposing the test sample to a hapten-analyte (H-A) conjugate, an anti-hapten antibody, and a common antibody pool to form a reaction mixture, wherein said common antibody pool comprises (1) at least two antisera, one of said at least two antisera containing an antibody αA, the other of said at least two antisera containing an antibody αB, or (2) at least one antisera and at least one monoclonal antibody, said at least one antisera containing an antibody αA and said monoclonal antibody being antibody αB, or (3) at least two monoclonal antibodies, one of said at least two monoclonal antibodies being antibody αA, the other of said at least two monoclonal antibodies being antibody αB, wherein antibody αA and antibody αB have different binding specificities for analyte (A), one of which antibodies αA or αB is also able to cross-react with other substances that are structurally related to analyte (A), while the other antibody cannot cross-react with said substances;

b) allowing the formation of complexes including (αH)(H-A)(αA), or (αH)(H-A)(αB), or (αH)(H-A)(αB)(αA), or combinations of the three; and c) detecting the presence or measuring the amount of any of (αH)(H-A)(αA), or (αH)(H-A)(αB) or (αH)(H-A)(αB)(αA), or combinations of the three in the absence or analyte (A); or the absence of (αH)(H-A)(αA), or (αH)(H-A)(αB), and (αH)(H-A)(αB)(αA) in the presence of analyte (A).

6. The immunoassay method of claim 5, wherein said anti-hapten antibody (αH) is attached to a particle, and agglutination of said particle indicates the presence of (αH)(H-A)(αA), or (αH)(H-A)(αB), or (αH)(H-A)(αB)(αA), or combinations of the three.

7. The immunoassay of claim 6, wherein said particle has a color providing detection of the complexes.

8. The immunoassay method of claim 7, wherein said particle is selected from the group consisting of: cells, polymeric microparticles, selenium microparticles, iron microparticles, and gold microparticles.

9. The immunoassay method of claim 8, wherein said cells are dyed erythrocytes.

10. The immunoassay method of claim 5, wherein said hapten-analyte conjugate (H-A), and said at least two antibodies (αA and αB) with different specificities for analyte (A) are in a liquid phase.

11. The immunoassay method of claim 5, wherein at least one of said antibodies with specificity for analyte (A) is a monoclonal antibody.

12. The immunoassay method of claim 5, wherein said analyte is selected from the group consisting of: haptens, antigens, and antibodies, wherein said haptens are not the same as those recognized by the anti-hapten antibodies coated on said particles, or the haptens in said hapten-analyte conjugates.

13. The immunoassay method of claim 5, wherein said analyte is a drug.

14. The immunoassay of claim 13, wherein said drug is a drug of abuse or a therapeutic drug, and are selected from the group consisting of: phencyclidines, opiates, cannabinoids, amphetamines, cocaines, and steriods.

15. The immunoassay method of claim 5, wherein said analyte is selected from the group consisting of toxins, vitamins, and hormones.

16. The immunoassay method of claim 5, wherein said analyte is an allergen.

17. The immunoassay method of claim 5, wherein said analyte is an enzyme.

18. The immunoassay method of claim 5, wherein said analyte is an antigen of a microorganism or tissue.

* * * * *